(12) United States Patent
Zhang et al.

(10) Patent No.: US 10,721,178 B2
(45) Date of Patent: Jul. 21, 2020

(54) SYSTEMS, APPARATUS AND METHODS FACILITATING DATA BUFFERING AND REMOVAL

(71) Applicant: Medtronic, Inc., Minneapolis, MN (US)

(72) Inventors: Bo Zhang, Blaine, MN (US); Nicholas C. Wine, Minneapolis, MN (US); Gary P. Kivi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 471 days.

(21) Appl. No.: 15/004,560

(22) Filed: Jan. 22, 2016

(65) Prior Publication Data

US 2017/0214631 A1     Jul. 27, 2017

(51) Int. Cl.

| | |
|---|---|
| *H04L 12/875* | (2013.01) |
| *G06F 3/06* | (2006.01) |
| *H04L 29/08* | (2006.01) |
| *H04W 28/02* | (2009.01) |
| *H04W 4/70* | (2018.01) |

(Continued)

(52) U.S. Cl.
CPC ........ *H04L 47/566* (2013.01); *A61N 1/37217* (2013.01); *A61N 1/37252* (2013.01); *G06F 3/067* (2013.01); *G06F 3/0608* (2013.01); *G06F 3/0619* (2013.01); *G06F 3/0647* (2013.01); *G06F 3/0652* (2013.01); *G16H 40/63* (2018.01); *G16H 40/67* (2018.01); *H04L 67/12* (2013.01);

(Continued)

(58) Field of Classification Search
CPC ...... H04L 47/566; H04L 67/12; H04W 4/005; H04W 28/0221; A61N 1/37217; A61N 1/37252; G06F 3/067; G06F 3/0652; G06F 3/0608; G06F 3/0619; G06F 3/0647

See application file for complete search history.

(56) References Cited

U.S. PATENT DOCUMENTS

| | | |
|---|---|---|
| 6,975,629 B2 | 12/2005 | Welin |
| 7,385,997 B2 | 6/2008 | Gorti et al. |

(Continued)

FOREIGN PATENT DOCUMENTS

WO     2007081829 A2     7/2007

OTHER PUBLICATIONS (PCT/US2017/014247) PCT Notification of Transmittal of the International Search Report and the Written Opinion of the International Searching Authority, dated May 10, 2017, 12 pages.

*Primary Examiner* — Anh Vu H Ly
*Assistant Examiner* — Hector Reyes

(57) ABSTRACT

Techniques for mitigating transmission of stale data from an implantable device are provided. In one embodiment, a method includes monitoring one or more data items stored in a data management queue prior to submission to a packet transmission queue for transmission as packets on a communication network to one or more other devices. The method also includes discarding a data item from the data management queue based on a determination that the data item has an expected arrival time to an other device that is after a latest acceptable arrival time associated with the data item. The method also includes estimating a size of the packet transmission queue, and transmitting another data item from the data management queue to the packet transmission queue based on a determination that the size of the packet transmission queue has a defined relationship to the threshold size.

25 Claims, 18 Drawing Sheets

(51) Int. Cl.
  *A61N 1/372* (2006.01)
  *G16H 40/67* (2018.01)
  *G16H 40/63* (2018.01)
(52) U.S. Cl.
  CPC ......... H04W 4/70 (2018.02); H04W 28/0221 (2013.01)

(56) References Cited

U.S. PATENT DOCUMENTS

| | | | |
|---|---|---|---|
| 7,457,243 | B2 | 11/2008 | Meggers et al. |
| 7,463,892 | B2 | 12/2008 | Eiger et al. |
| 7,872,968 | B2 | 1/2011 | Gorti et al. |
| 7,899,069 | B2 | 3/2011 | Gorti et al. |
| 9,036,624 | B2 | 5/2015 | Sabella et al. |
| 9,288,614 | B1* | 3/2016 | Young ................ A61N 1/37252 |
| 9,687,658 | B2 | 6/2017 | Wu et al. |
| 9,855,433 | B2 | 1/2018 | Shahandeh et al. |
| 2006/0164979 | A1* | 7/2006 | Pirbhai .................. H04L 43/02 370/229 |
| 2009/0063187 | A1 | 3/2009 | Johnson et al. |
| 2009/0245104 | A1* | 10/2009 | Nishimura ............. H04L 47/10 370/230 |
| 2011/0158206 | A1 | 6/2011 | Shrestha et al. |
| 2011/0172550 | A1* | 7/2011 | Martin ................. A61B 5/7445 600/523 |
| 2011/0184491 | A1* | 7/2011 | Kivi .................... A61N 1/37276 607/60 |
| 2012/0108922 | A1 | 5/2012 | Schell et al. |
| 2012/0172690 | A1 | 7/2012 | Anderson et al. |
| 2012/0172941 | A1 | 7/2012 | Rys |
| 2013/0196703 | A1 | 8/2013 | Masoud et al. |
| 2013/0214909 | A1 | 8/2013 | Meijers et al. |
| 2014/0163162 | A1* | 6/2014 | Wade .................... B01F 3/0803 524/563 |
| 2014/0169162 | A1 | 6/2014 | Romano et al. |
| 2014/0188348 | A1 | 7/2014 | Gautama et al. |
| 2014/0214104 | A1 | 7/2014 | Greenhut et al. |
| 2014/0330327 | A1 | 11/2014 | Thompson-Nauman et al. |
| 2015/0133951 | A1 | 5/2015 | Seifert et al. |
| 2015/0271255 | A1* | 9/2015 | Mackay ................ H04L 67/101 709/226 |
| 2015/0341785 | A1 | 11/2015 | Young et al. |
| 2017/0026777 | A1 | 1/2017 | Denboer et al. |

* cited by examiner

SYSTEMS, APPARATUS AND METHODS FACILITATING DATA BUFFERING AND REMOVAL

TECHNICAL FIELD

This disclosure relates generally to implantable devices and, more particularly, to systems, apparatus, methods and computer-readable storage media facilitating data buffering and removal in implantable devices.

BACKGROUND

Contemporary healthcare relies heavily on implantable medical devices (IMDs) to help patients lead normal and healthy lives. For example, IMDs such as pacemakers, implantable cardioverter-defibrillators (ICDs), cardiac re-synchronization therapy (CRT) devices, drug delivery systems, and neurostimulators can help manage a broad range of ailments, such as cardiac arrhythmia, diabetes, and Parkinson's disease. Modern IMDs are entrusted with important tasks such as measuring and collecting data about vital signs and facilitating the provisioning of the collected data to devices utilized by doctors and nurses. Accordingly, telemetry has an important role in accomplishing these important tasks. However, the collected data can be time-sensitive and, therefore, systems, apparatus, methods and computer-readable storage media that facilitate data buffering and removal of stale data prior to transmission are desired.

SUMMARY

The following presents a simplified summary to provide a basic understanding of one or more embodiments described herein. This summary is not an extensive overview of the embodiments envisaged herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include systems, apparatus, methods and computer-readable storage media facilitating mitigation of transmission of stale data from an implantable device. In some embodiments, the implantable device is or includes an IMD. In other embodiments, the implantable device is or includes a device configured to interact with the IMD. In these embodiments, both the implantable device and the IMD can be implanted within and/or disposed on a patient. In various embodiments, the patient can be any living being (e.g., a human, an animal).

In an embodiment, an implantable device is provided that includes: a memory that stores executable components; and a processor that executes the executable components stored in the memory. The executable components include a communication component configured to transmit one or more packets on a communication network, a packet transmission queue configured to store the one or more packets for transmission on the communication network, and a data management queue configured to store one or more data items for submission to the packet transmission queue to one or more other devices. The executable components also include a data removal component configured to remove a data item of the one or more data items from the data management queue, wherein removal is based on a determination that the data item in the data management queue has an expected arrival time to another device of the one or more other devices that exceeds a latest arrival time associated with the data item.

In some embodiments, the implantable device also includes a data forwarding component configured to determine a size of the packet transmission queue, and in response to the size of the packet transmission queue being within a threshold size, forward another data item from the data management queue to the packet transmission queue.

In some embodiments, the implantable device also includes a deadline component configured to determine the deadline for the data item based on a characteristic associated with the implantable device, a characteristic associated with the other device, a type of data of the data item, or a status of the implantable device.

In another embodiment, a method includes providing, by an implantable device including a processor, one or more data items in a data management queue for buffering prior to submission to a packet transmission queue for transmission as one or more packets on a communication network to one or more other devices. The method also includes removing a data item from the data management queue based on a determination that the data item of the one or more data items in the data management queue has an expected arrival time to another device of the one or more other devices that is after a defined maximum acceptable arrival time associated with the data item.

In some embodiments, the method includes estimating the expected arrival time of the data item to the other device based on an expected transmission time per packet in the packet transmission queue.

In another embodiment, a non-transitory computer-readable storage medium is provided. The non-transitory computer-readable storage medium stores executable instructions that, in response to execution, cause an implantable device including a processor to perform operations. The operations include monitoring one or more data items stored in a data management queue prior to submission of the one or more data items to a packet transmission queue for transmission as one or more packets on a communication network to one or more other devices. The operations also include discarding a data item of the one or more data items from the data management queue, wherein the discarding is associated with a determination that the data item has an expected arrival time to another device of the one or more other devices that is after a defined latest arrival time for the data item.

In some embodiments, the operations also include reducing a rate of transferring the one or more data items to the data management queue based on a determination that a size of the data management queue exceeds a threshold queue size.

In another embodiment, a system is provided. The system includes a sensor and an implantable device. The implantable device includes a detection component configured to detect a signal from the sensor and supply a data item of one or more data items and corresponding to the signal to a data management queue for transmission to another device. The implantable device also includes a data removal component configured to discard the data item from the data management queue based on a determination that the data item in the data management queue is estimated to arrive at the other device after an acceptable latest arrival time associated with the data item.

In some embodiments, the implantable device also includes a throttling component configured to reduce a sampling rate of the signal to reduce a number of the one or more data items to be supplied to the data management queue.

In some embodiments, the system also includes the other device. The other device can include a mobile device in some embodiments. In some embodiments, the system also includes a server device configured to receive the data item, or information about the data item, from the other device.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures can depict example arrangements of components, additional and/or intervening components can be present in one or more embodiments.

Further, while embodiments described herein variously reference an implantable device or an IMD as implanted or located within a patient or a body or worn by a patient or a body, it is noted and should be understood that in any of these embodiments, the implantable device or the IMD referenced can be implanted or located within the patient or body and/or coupled to or disposed on an exterior surface of the patient or body as appropriate relative to the specific embodiments. All such variations are envisaged and intended to be encompassed herein.

Some examples herein are described using BLUETOOTH® Low Energy (BLE) protocol for communication between external device 116 and implantable device 104 for illustrative purposes. However, any suitable communication protocol for communication between external device 116 and implantable device 104 is intended to be encompassed herein, examples of which are discussed below.

Figure 1:
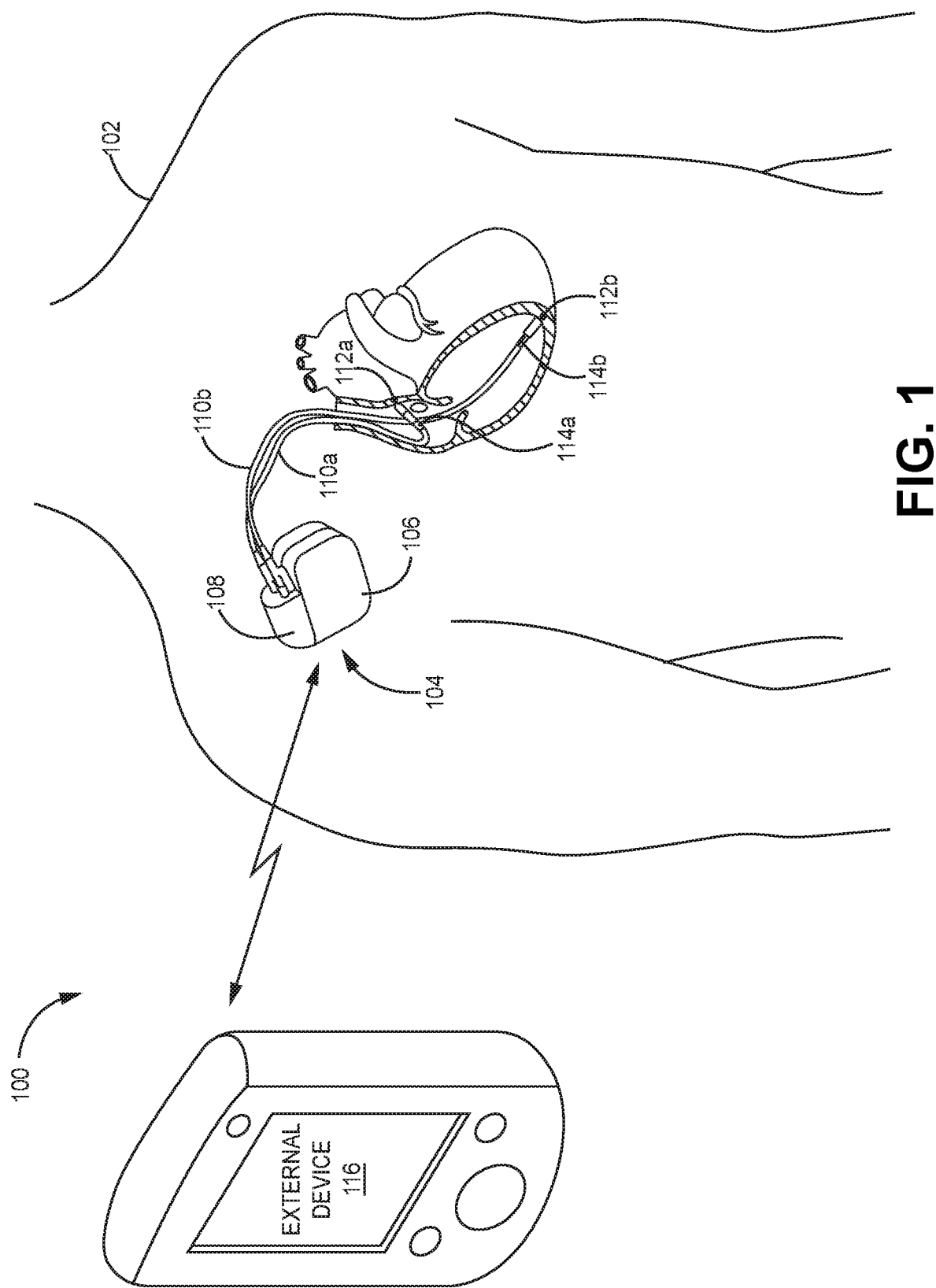
FIG. 1 illustrates a schematic diagram of an example, non-limiting medical device telemetry system facilitating management of transmission of data from an implantable device to an external device in accordance with one or more embodiments described herein.

With reference now to the drawings, FIG. 1 illustrates a schematic diagram of an example, non-limiting medical device telemetry system 100 facilitating management of transmission of data from an implantable device to an external device in accordance with one or more embodiments described herein. System 100 includes implantable device 104, which can be configured to mitigate transmission of stale data (e.g., one or more data items). In the embodiment shown, medical device telemetry system 100 includes implantable device 104 implanted within a body 102, and an external device 116. In some embodiments, the implantable device 104 is an IMD that is also configured to facilitate one or more diagnostic or treatment functions relative to the body 102. In some embodiments, the implantable device 104 is separate from an IMD (not shown in this embodiment) that is also implanted within the body 102 and communicatively and/or electrically coupled to the IMD.

Examples of devices, apparatus and systems herein can include one or more computer-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. Implantable device 104 can include memory (not shown) that stores computer-executable components and instructions. Implantable device 104 can also include a processor (not shown) configured to facilitate operation of the instructions (e.g., computer-executable components and instructions) by implantable device 104.

One or more embodiments of medical device telemetry system 100 are described in connection with managing transmission of stale data by implantable device 104 in association with performing telemetry communication with one or more external devices, such as external device 116. In particular, implantable devices can use wireless telemetry to exchange various types of information with external devices. For example, using wireless telemetry, an external device 116 can read data captured by the implantable device 104 (e.g., electrocardiogram data) or send configuration information to the implantable device 104. The implantable device 104 can also transmit sensed physiological data, diagnostic data determined based on the sensed physiological data, and/or implantable device 104 performance data to the external device 116. Data associated with the implantable device 104 can be provided to a wide variety of external devices, including, but not limited to, a mobile device (e.g., tablet computer, smartphone) associated with a patient or a physician, a medical device associated with a patient or a physician, an electronic device at a home of a patient or at an office of a physician, an off-the-shelf device purchased at a store, etc.

In various embodiments, the implantable device 104 and/or the external device 116 can communicate employing proprietary and/or commercially available public communication protocols. By way of example, but not limitation, the communication protocols can include, but are not limited to, BLUETOOTH®, BLUETOOTH® low energy (BLE), near field communication (NFC), Wireless Fidelity (Wi-Fi) protocol, Zigbee®, RF4CE, WirelessHART, 6LoWPAN, Z-Wave, ANT, and the like.

As commercially available communication protocols are more frequently employed to conduct telemetry with an implantable device 104, data transmission from implantable device 104 to external device 116 can be delayed resulting in transmission of stale data (e.g., data that arrives at external device 116 after a particular deadline). As a result, implantable device 104 and external device 116 can waste resources transmitting and receiving stale data that may be unable to be used by external device 116 and therefore discarded by external device 116.

For example, according to various commercially available communication protocols (e.g., BLE) to begin a telemetry session with implantable device 104, external device 116 can send a connection request to the implantable device 104 requesting to establish a telemetry session. Upon reception of the connection request by the implantable device 104, an initial telemetry connection can be established between the implantable device 104 and the external device 116. For example, the implantable device 104 and the external device 116 can begin a pairing process that is used to establish a secure or trusted telemetry session between the implantable device 104 and the external device 116.

Implantable device 104 can then transmit sensed physiological data, diagnostic determinations made based on the sensed physiological data, and/or other data. Some of the data can be captured at body 102 by implantable device 104 and transmitted to external device 116. In some embodiments, to transmit the data, a device configured to transmit over a communication layer (e.g., BLE link layer) in implantable device 104 can place the packets in a packet transmission queue (e.g., BLE link layer queue) of the implantable device 104. Some communication protocols (e.g., BLE) will continue to try to re-transmit a packet until the packet is successfully transmitted to external device 116. This process of attempting re-transmissions can cause other packets in the packet transmission queue to be delayed, potentially beyond a timeframe in which the data within the packets are useful to external device 116. For example, real-time waveform data from a cardiac implantable medical device can have a deadline set at a defined amount of time (e.g., 300 milliseconds (ms)) for arrival at the external device. If the waveform data arrives at external device 116 after 300 ms from when the waveform data was generated based on the sensed characteristic of the body 102, external device 116 can discard (e.g., ignore, not process, flush, or delete) the waveform data as being stale.

In accordance with various embodiments, system 100 provides techniques for managing transmission of data by implantable device 104 to minimize or prevent the transmission of stale data to external device 116 as discussed below.

In an embodiment, following reception, by implantable device 104, of a connection request from an external device 116, implantable device 104 can establish a secured telemetry connection with the external device 116.

Implantable device 104 can be configured to initiate transmission of sensed and/or stored data to external device 116. In various embodiments, the implantable device 104 can initiate the transmission of the data automatically upon detecting or sensing the data or generating the waveform data and/or in response to a request by external device 116.

As used herein, the term "data" can refer to any type of data (e.g., ECG data, ICD data, previously stored data, data generated within a defined amount of time prior to transmission, real-time data, non-real-time data) in any number of different formats (e.g., waveform data, discrete signals) and whether the data has time constraints that call for delivery and/or external device 116 reception within a defined amount of time (e.g., real-time data) or data with no time constraints on delivery or reception. All such embodiments are envisaged. By way of example, but not limitation, in different embodiments, the data can be, but is not limited to, data sensed in response to the request, data having a deadline for transmission to (or receipt by) external device 116, data continually sensed and having a deadline for transmission to external device 116, or data that is transmitted after being sensed. Furthermore, data can include stored interrogation data, such as, in a non-limiting example, patient name, patient identifier, patient medical history, patient emergency contact information, device parameters, stored sensed data, or any other suitable data that can be stored in the implantable device 104. In order to minimize or prevent the transmission of data to external device 116 beyond a deadline assigned to the data, implantable device 104 can employ a data management queue coupled to the packet transmission queue. Implantable device 104 can monitor a size of the packet transmission queue and forward data from the data management queue to the packet transmission queue if the size of the packet transmission queue is within a threshold size.

In some embodiments, implantable device 104 can monitor the data management queue to identify data that is estimated to arrive at external device 116 beyond a deadline assigned to the data (i.e. stale data), and discard the stale data (to avoid or reduce the use of implantable device 104 resources that would otherwise be employed for further processing and/or transmission of the stale data). In some embodiments, implantable device 104 can assign different deadlines to different types of data based upon the type of data (e.g., ECG, pulse oximeter, glucose, blood pressure, heart rate, respiratory rate, neural data), the type of implantable device 104, the type of body 102 in which the implantable device is implanted, the type of external device 116, a type of environment in which external device 116 is located (e.g., physician's office, home, emergency room, operating room, ambulance, hospital, or any other suitable location), a specification from external device 116, or any other suitable criteria for assigning deadlines to data delivery.

In some embodiments, implantable device 104 can assign different priorities to different types of data based upon the type of data (e.g., ECG, pulse oximeter, glucose, blood pressure, heart rate, respiratory rate, neural data, interrogation data, sensed data, stored data, or any other suitable type of data), the type of implantable device 104, the type of body in which the implantable device is implanted, the type of external device 116, a type of environment in which external device 116 is located (e.g., physician's office, home, emergency room, operating room, ambulance, hospital, or any other suitable location), a specification from external device 116, or any other suitable criteria for assigning priorities to data.

Implantable device 104 is configured to process information to make determinations regarding selection of data to forward from the data management queue to the packet transmission queue based on a function of deadline and/or priority as is discussed in more detail with reference to FIG. 3. Moreover, implantable device 104 can throttle (e.g., adjust sampling rate of data, adjust channels of data, or adjust types of data) to increase or decrease data being placed into the data management queue to minimize or prevent the transmission of stale data to external device 116 as discussed in more detail below.

It is to be appreciated that the implantable device 104 can include one or more devices, transducers and/or circuits that can facilitate telemetry communication and disablement of telemetry communication. For example, the implantable device 104 can include a transmitter that transforms electrical power into a signal associated with transmitted data packets. Additionally, the implantable device 104 can include one or more devices, transducers and/or circuits that can facilitate receiving information from one or more devices (e.g., the external device 116, a server device, etc.). For example, the implantable device 104 can include a receiver that transforms a signal into electrical power.

In the embodiment shown in medical device telemetry system 100, a user operating the external device 116 is a patient in which the implantable device 104 is implanted. In another embodiment, another person (e.g., such as medical caregiver) interacting with the patient in which the implantable device 104 is implanted can operate the external device 116 outside the body 102 in which the implantable device 104 is located. Implantable device 104 can include any number of different types of implantable devices configured to communicate with the external device 116 or another external device. The particular, size, shape, placement and/or function of the implantable device 104 may not be critical to the subject disclosure in some embodiments.

In an embodiment, implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, implantable device 104 can be or include any number of other types of implantable devices that are not IMDs.

For exemplary purposes, implantable device 104 is illustrated in medical device telemetry system 100 as an IMD implanted within the chest of a body 102 of a patient and configured to provide medical treatment associated with a heart disease or condition (e.g., an implantable cardioverter-defibrillator (ICD) and/or a pacemaker). In addition to the medical treatment, implantable device 104 can also be configured to provide the data packetizing and communication operations described herein. Implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMS) device), or an induction component. The various embodiments described herein can provide improved management of power associated with the one or more power sources, for example, by mitigating resources spent on transmission of stale data.

The electrical components can vary depending on the particular features and functionality of implantable device 104. In various embodiments, these electrical components can include, but are not limited to, one or more processors, memories, transmitters, receivers, transceivers, sensors, sensing circuitry, therapy circuitry, antennas and other components. In some embodiments, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, implantable device 104 is also an IMD and further includes leads 110a and 110b connected to the housing 106. The leads 110a and 110b extend into the heart and respectively include one or more electrodes. For example, as depicted in medical device telemetry system 100, leads 110a and 110b each include a respective tip electrodes 112a and 112b and/or ring electrodes 114a and 114b located near a distal end of their respective leads 110a and 110b. When implanted, tip electrodes 112a and 112b and/or ring electrodes 114a and 114b are placed relative to or in a selected tissue, muscle, nerve or other location within the body 102 of the patient. As depicted in medical device telemetry system 100, tip electrodes 112a and 112b are extendable helically shaped electrodes to facilitate fixation of the distal end of leads 110a and 110b to the target location within the body 102 of the patient. In this manner, tip electrodes 112a and 112b are formed to define a fixation mechanism. In other embodiments, one or both of tip electrodes 112a and 112b can be formed to define fixation mechanisms of other structures. In other instances, leads 110a and 110b can include a fixation mechanism separate from tip electrodes 112a and 112b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a and 110b are connected at a proximal end of the implantable device 104 via connector block 108. Connector block 108 can include one or more receptacles that interconnect with one or more connector terminals located on the proximal end of leads 110a and 110b. Leads 110a and 110b are ultimately electrically connected to one or more of the electrical components within housing 106. One or more conductors (not shown) extend within leads 110a and 110b from connector block 108 along the length of the lead to engage the ring electrodes 114a and 114b and tip electrodes 112a and 112b, respectively. In this manner, each of tip electrodes 112a and 112b and ring electrodes 114a and 114b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors can electrically couple to circuitry, such as a therapy module or a sensing module, of the implantable device 104 via connections in connector block 108.

In one or more embodiments, the implantable device 104 is configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112a and 112b and 114a and 114b. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other embodiments, the implantable device 104 can include more or fewer leads extending from the housing 106. For example, the implantable device 104 can be coupled to three leads, e.g., a third lead implanted within a left ventricle of the heart of the patient. In another embodiment, the implantable device 104 can be coupled to a single lead that is implanted within the ventricle of the heart of the patient. In other embodiments, the lead can be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads can include more or fewer electrodes. In instances in which the implantable device 104 is used for therapy other than pacing, (e.g., defibrillation or cardioversion), the leads can include elongated electrodes, which can, in some instances, take the form of a coil. The therapy circuitry of the implantable device 104 can generate and deliver defibrillation or cardioversion shocks to the heart via any combination of the elongated electrodes and housing electrode. The therapy circuitry may include one or more HV output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 can include no leads, as in the case of an intracardiac pacemaker or a leadless pressure sensor. In the case of an intracardiac pacemaker, the device can include a housing sized to fit wholly within the patient's heart. In one embodiment, the housing can have a volume that is less than 1.5 cc and, more preferably, less than 1.0 cubic centimeter (cc). However, the housing can be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

Implantable device 104 can include various different types of sensors, electrodes and/or circuitry configured to detect one or more signals associated with a physiological state within the body 102 of the patient, motion of the body 102 of the patient, or sound or speech generated or detected within the body 102 of the patient. In some embodiments, the physiological state can include a function of the body 102 and/or a condition of the body 102. These sensors, electrodes and/or circuitry can include, but are not limited to, sensors, electrodes and/or circuitry configured to detect blood pressure, blood flow rate, heart rate, respiratory rate, blood composition, substances within the blood (e.g., oxygen, carbon dioxide or glucose), temperature, patient activity state (e.g., moving, still, asleep, awake or exercising), speech and/or other physical properties associated with the patient. As implantable device 104 is illustrated in system 100, by way of example, these sensors and/or circuitry can be included within the housing 106 and/or included on or in association with the various leads 110a and 110b, tip electrodes 112a and 112b and ring electrodes 114a and 114b of the implantable device 104. For example, in addition to tip electrodes 112a and 112b and ring electrodes 114a and 114b, implantable device 104 can include one or more additional sensors (not shown) that include, but are not limited to, pressure sensors, blood flow sensors, force sensors, blood composition sensors, optical sensors, accelerometers, piezoelectric sensors, biosensors, acoustic sensors and/or other sensors configured to detect states and/or physical activity of the body 102.

A sensor as described herein can include hardware (e.g., sensor hardware components, sensor circuitry or a processor), software (e.g., computer-executable instructions configured to facilitate processing of sensed data), or a combination of hardware and software configured to detect (e.g., by sensing, detection or measurement) a property (e.g., physiological property) associated with the body 102 in which the implantable device 104 is located, and/or configured to record, indicate or otherwise respond to the detected property.

In an embodiment, implantable device 104 can include various different types of sensors, and/or circuitry configured to detect information associated with the heart rhythm. The information detected can be processed in various embodiments. For example, the implantable device 104 can include hardware, software, or a combination of hardware and software, that is configured to measure electrical activity of the heart. An electrocardiogram (ECG) is an example of a device that can be employed by the implantable device 104 to record the electrical activity of the heart over a defined period of time, as detected by one or more electrodes (e.g., tip electrodes 112a and 112b or ring electrodes 114a and 114b) connected to one or more parts of the body 102 (e.g., cardiac tissue inside the body 102, skin of the chest outside the body 102 and/or near the heart). An ECG detects electrical impulses generated by the polarization and depolarization of cardiac tissue and translates the impulses into a waveform that corresponds to the rate and regularity of beats of the heart.

In another embodiment, the implantable device 104 can include or be associated with a device (e.g., pulse oximeter) that is configured to detect variation in blood oxygenation level that can be correlated to pulse rate. A pulse oximeter can indirectly monitor the oxygen saturation of the blood in body 102 (as opposed to measuring oxygen saturation directly through a blood sample). The pulse oximeter can utilize the light absorptive characteristics of hemoglobin and the pulsating nature of blood flow through the body 102 to aid in determining the oxygenation status in the body 102. First, there is a color difference between arterial hemoglobin saturated with oxygen, which is bright red, and venous hemoglobin without oxygen, which is dark red. Second, with each pulsation or heartbeat there is generally a slight increase in the volume of blood flowing through the arteries. Because of the increase of blood volume, albeit small, there is generally an associated increase in oxygen-rich hemoglobin. A PPG can be generated based on the amount of oxygen-rich hemoglobin pulsating through the blood vessel volume.

In another embodiment, implantable device 104 can include a transmittance pulse oximeter. The transmittance pulse oximeter can include a photodetector, a light source, and a circuit that produces, collects, and processes photoplethysmographic signals. Implantable device 104 can activate the transmittance pulse oximeter to generate two wavelengths of light through a part of the body 102 and that is detected by the photodetector. The photodetector can measure the changing absorbance at each of the wavelengths in response to transmittance of the light wavelengths through the body 102. Based on the changes in absorbance, the transmittance pulse oximeter can determine the pulse rate of the patient.

In another embodiment, implantable device 104 can include a reflectance pulse oximeter to determine pulse rate of the body 102. The reflectance pulse oximeter can also include a photodetector, a light source, and a circuit that produces, collects, and processes PPG signals. With a reflectance pulse oximeter, the incident light is passed through the body and is reflected from the subcutaneous tissue and bone back to the photodetector.

In one or more embodiments described herein, an external device 116 can communicate with the implantable device 104 to exchange data with the implantable device 104. For example, the external device 116 can read data captured by the implantable device 104 (e.g., electrocardiogram (ECG) data) and/or remotely control the implantable device 104 (e.g., to adjust sensing, pacing therapy and/or defibrillation therapy). In one example, the external device 116 can remotely control the implantable device 104 by programming the implantable device 104. The implantable device 104 can also transmit to external device 116 sensed physiological data, diagnostic determinations made based on the sensed physiological data, implantable device 104 performance data and/or implantable device 104 integrity data.

External device 116 can include any suitable computing device configured to communicate with implantable device 104. In some embodiments, the external device 116 can be a remote electronic device. For example, external device 116 can include, but is not limited to, a handheld computing device, a mobile phone, a smart phone, a tablet personal computer (PC), a laptop computer, a desktop computer, a personal digital assistant (PDA), a server device, a monitor, a display, a scope, and/or a wearable device. In some embodiments, the external device 116 can include a display that can present information associated with the implantable device 104. In another embodiment, the external device 116 can include an application and/or a program associated with the implantable device 104.

Figure 2:
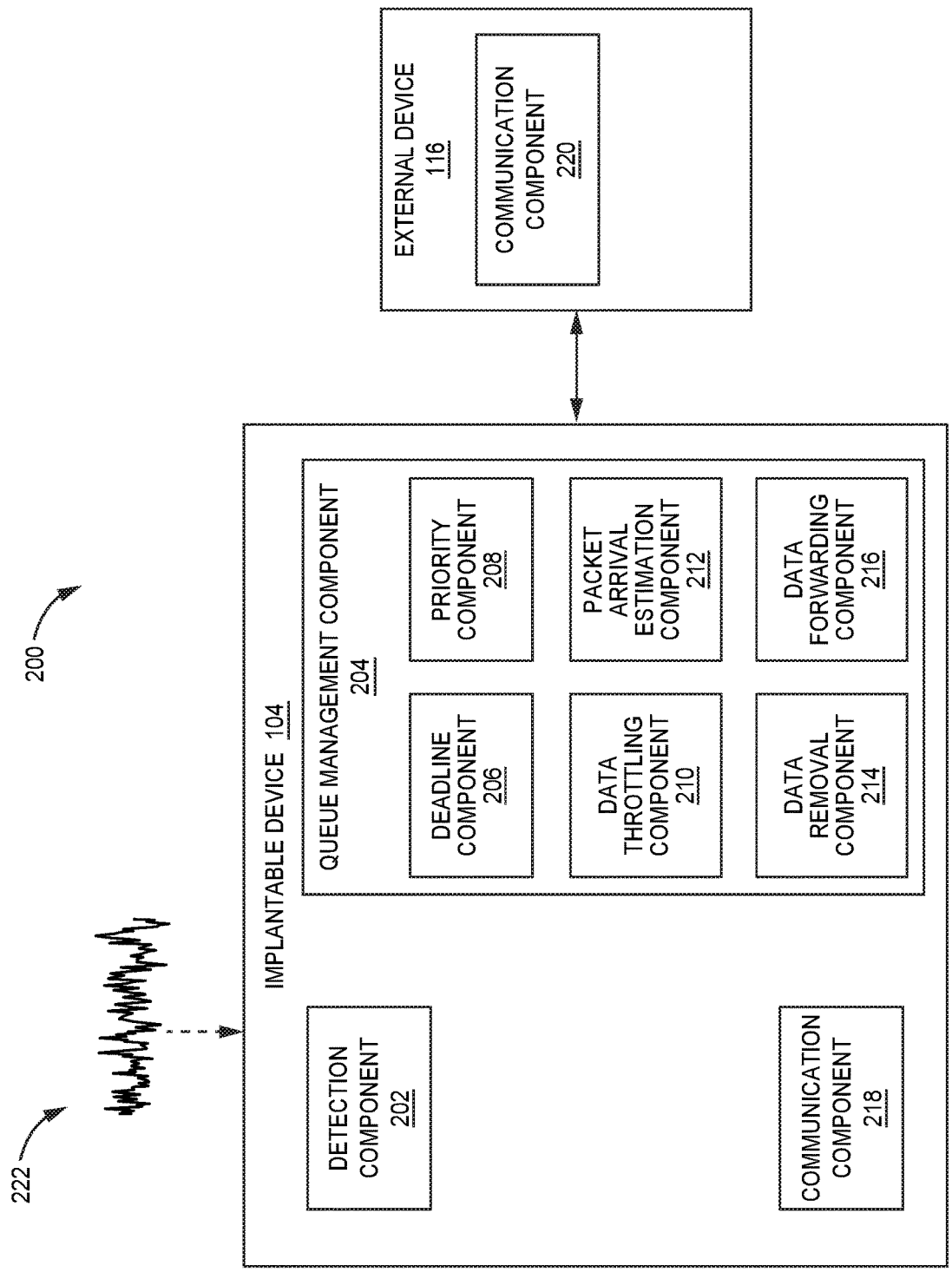
FIG. 2 illustrates a block diagram of an example, non-limiting medical device telemetry system facilitating management of transmission of data from an implantable device to an external device to mitigate transmission of stale data in accordance with one or more embodiments described herein.

FIG. 2 illustrates a block diagram of an example, non-limiting medical device telemetry system facilitating management of transmission of data from an implantable device to an external device to mitigate transmission of stale data in accordance with one or more embodiments described herein. In some embodiments, the medical device telemetry system 200 can be configured to facilitate management of transmission of data (e.g., real-time generated data, non-real-time generated data or stored data) from an implantable device to an external device in accordance with descriptions of system 100 described herein. Repetitive description of like elements employed figures described herein is omitted for sake of brevity.

Similar to system 100, system 200 includes external device 116 and implantable device 104. Although not shown, it is to be appreciated that the implantable device 104 is implanted within or provided on a body of a living being (e.g., body 102 of FIG. 1).

As depicted in system 200, implantable device 104 is configured to employ detection component 202 to perform detecting of signal 222, such as through various sensors. As discussed supra, in one or more embodiments, signal 222 can include different information associated with a physiological state of a body with which the implantable device 104 is associated. For example, signal 222 can represent raw data that can be correlated to a heart rate, ventilation rate and/or blood pressure. This raw data can vary depending on the implementation of system 200 and the detection component 202 employed by implantable device 104. For example, in embodiments in which detection component 202 is configured to detect signals associated with heart rate using an ECG device, signal 222 can include information corresponding to electrical activity of the heart.

In another embodiment, signal 222 can include raw motion data based on motion of the body with which the implantable device 104 is associated. For example, signal 222 generated by the implantable device 104 can vary in response to movement of the body. Accordingly, signal 222 can include first motion data (e.g., velocity measurements, acceleration measurements or displacement measurements) corresponding to motion of implantable device 104 in response to movement of the body.

In some embodiments, signal 222 can include raw data that can be generated based on a walking motion, a lying down motion (or position), a jumping motion, a spinning motion, a hand raising motion, etc, made by the body in which the implantable device 104 is implanted. This raw data can vary depending on the implementation of system 200 and/or the detection component 202 employed by implantable device 104. For example, when detection component 202 is configured to detect motion signals using a piezoelectric device, signal 222 can include information corresponding to changes in pressure, acceleration, strain or force experienced by the implantable device 104.

In yet another embodiment, signal 222 can include raw data corresponding to a sound that is detected by detection component 202. In one example, the detected sound includes a voice sound made by the body in which the implantable device 104 is implanted. In another embodiment, the detected sound can include a sound made by another device, person, object, etc. Accordingly, the data of raw signal 222 can vary depending on the implementation of system 200 and the detection component 202 employed by implantable device 104.

In another embodiment, when detection component 202 is configured to employ acoustic sensors, signal 222 can include sound waves received or detected at implantable device 104 (e.g., through the body). In another embodiment, when the detected sound includes a voice sound made by the body in which the implantable device 104 is implanted, signal 222 can also include vibration data corresponding to vibration of the vocal cords during production of the sound.

It is to be appreciated that any suitable signal 222 detectable by implantable device 104 is intended to be encompassed herein. Furthermore, implantable device 104 can be a multi-function device capable of detecting a variety of signals associated with different areas and/or functions of the body as described herein. Additionally, detection component 202 can apply timestamps to data associated with signals 222. Deadlines can be based on the timestamps. For example, if data has a timestamp TS, then the deadline can be an amount of time added to timestamp TS, or can be a specific time after timestamp TS, or can be any other suitable mechanism for specifying a deadline in relation to timestamp TS.

External device 116 and implantable device 104 can include communication components 220 and 218, respectively. In various embodiments, communication components 218 and 220 are configured to facilitate communication between external device 116 and implantable device 104. For example, communication components 218 and 220 can include or be various hardware and/or software devices or components associated with establishing and/or conducting a telemetry session between external device 116 and implantable device 104.

Communication components 218 and 220 can be configured to communicate using various wireless communication protocols. For example, communication components 218 and 220 can include a transmitter and/or receiver configured to transmit and/or receive electrical wireless or wired signals. In some embodiments, communication components 218 and 220 can be configured to communicate using various wireless communication protocols including, but not limited to, near field communication (NFC), BLUETOOTH® technology, ZigBee®, radio frequency (RF) communications, SIP-based communications, cellular communication, an ultra-wideband (UWB) technology-based protocol, a radio frequency (RF) communication-based protocol, or other forms of communication including both proprietary and non-proprietary communication protocols.

External device 116 can transmit (e.g., using communication component 220), a request message to the implantable device 104 requesting a telemetry session between the external device 116 and the implantable device 104. For example, this request message can be generated and sent in response to input received at the external device 116 requesting pairing between the implantable device 104 and the external device 116. It is to be appreciated that implantable device 104 can also initiate pairing or communication with external device 116 without receipt of the request from the external device 116.

Communication component 220 can employ a particular frequency (e.g., a non-commercial frequency) to send the request message as an RF data signal that is recognizable by the implantable device 104 as a request to pair with the implantable device 104. In some embodiments, in response to transmission of the RF data signal by the external device 116 and reception and identification of the RF data signal by the implantable device 104 (e.g., via communication component 218), implantable device 104 and external device 116 can pair and establish a telemetry session.

In some embodiments, in response to transmission of the RF communication signal by the external device 116 and reception and identification of the RF data signal by the implantable device 104, the implantable device 104 can send an acknowledgment message (e.g., using an RF data signal) back to the external device 116 acknowledging receipt of the request. In response to sending the acknowledgment message, implantable device 104 can activate detection component 202 to begin detecting signal 222 for a defined detection period (e.g., for one minute after sending the acknowledgment message or any other suitable period of time). The defined detection period can be determined by implantable device 104, or by external device 116 and communicated to implantable device 104.

After or during detecting of signal 222, implantable device 104 can employ communication component 218 to communicate data to external device 116 representative of signal 222. In one embodiment, for example, signal 222 can include data identifying voltage variations associated with electrical impulses in cardiac tissue. Signal 222 can include similar raw data or another form of raw data associated with a heart rhythm. Implantable device 104 can receive signal 222. In this embodiment, a sensor can detect and/or generate the signal 222. In some embodiments, the signal 222 is not received by implantable device but is generated by implantable device 104 (based on detection with a sensor within implantable device 104, for example).

Detection component 202 can process raw data of signal 222 and package and/or transform the data for transmission to external device 116. For example, signal 222 can include data from various leads to the heart associated with ECG. Detection component 202 can transform signal 222 into data for transmission to external device 116. In some embodiments, the data can be waveform and/or marker data. It is to be appreciated that detection component 202 can also detect signal 222 over time and store all or a portion of the data associated with signal 222 for transmission to external device 116 as historical data. In some embodiments, data that is historical data is non-real-time data. In some embodiments, detection component 202 can store information about one or more events detected and indicated by signal 222. The information can include, but is not limited to, as abnormal readings (e.g., the case when signal 222 indicates an event that is not within a specified threshold), samples of events (e.g., the samples can be taken at regular or irregular intervals).

Implantable device 104 can include a queue management component 204 that manages queuing (e.g., buffering) and/or discarding of data for transmission 312 in implantable devices. Queue management component 204 can include deadline component 206, which can be configured to assign one or more deadlines to data for transmission from implantable device 104. In some embodiments, queue management component 204 can include priority component 208. Priority component 208 can be configured to assign one or more priorities to data for transmission from implantable device 104. It is to be appreciated that different data can have different permutations of deadlines and priorities. For example, different data can have the same deadline but different priorities, the same deadline and priority or the same priority but different deadlines.

As shown, queue management component 204 can also include data throttling component 210, which can be configured to throttle data to increase or decrease data being placed into the data management queue, which is shown and described in greater detail with reference to FIG. 3. In various embodiments, throttling data can include, but is not limited to, adjusting the sampling rate of data, adjust one or more channels of data, or adjust types of data.

Figure 3:
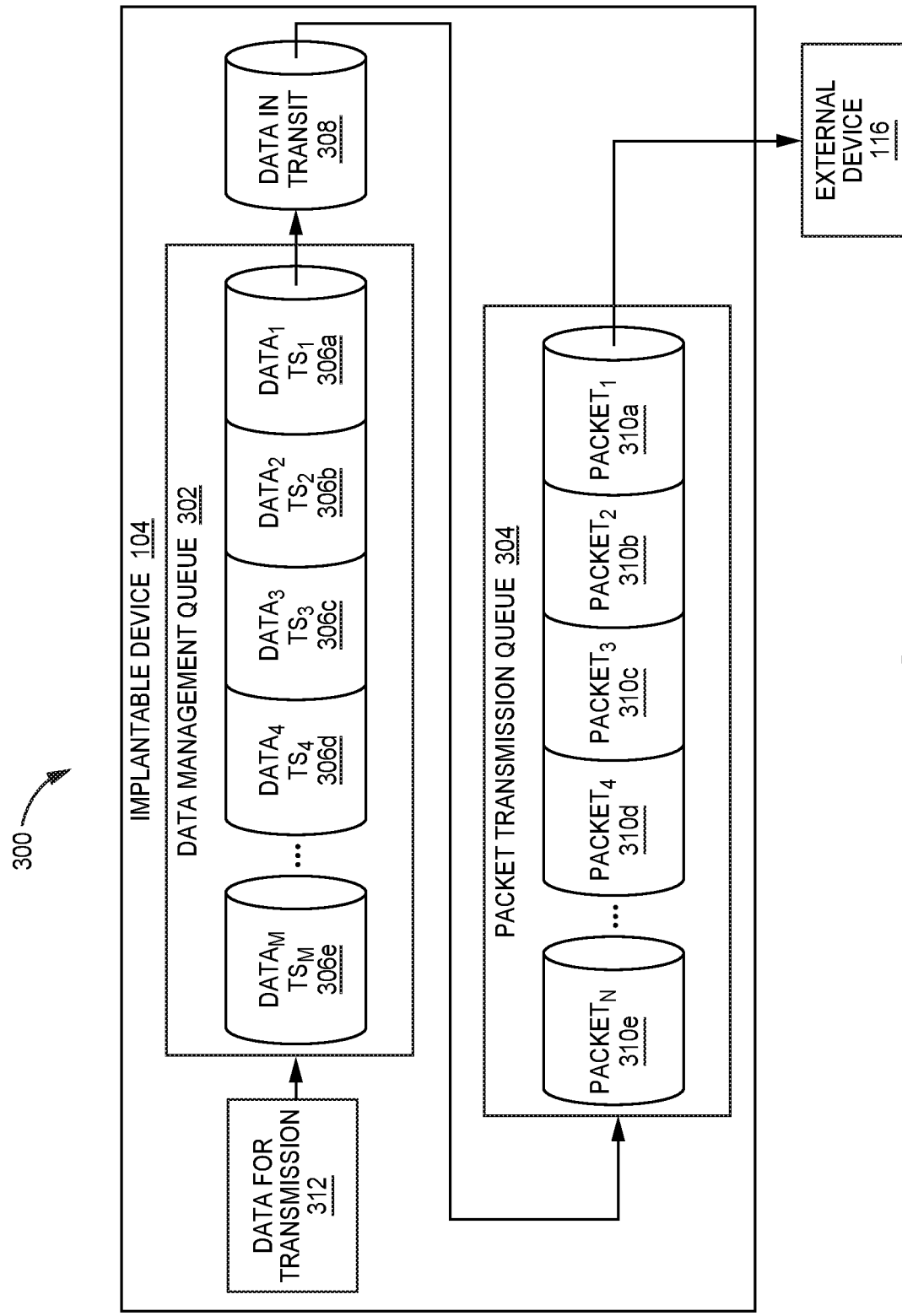
FIG. 3 illustrates a block diagram of an example, non-limiting medical device telemetry system facilitating management of transmission of data from an implantable device to an external device to mitigate transmission of stale data employing a data management queue in accordance with one or more embodiments described herein.

Queue management component 204 can also include packet arrival estimation component 212, which can be configured to estimate an arrival time to external device 116 of data in data management queue (e.g., data management queue 302 of FIG. 3).

Queue management component 204 can also include data removal component 214. The data removal component 204 can be configured to remove data from data management queue (e.g., data management queue 302 of FIG. 3) that is estimated by packet arrival estimation component 212 to arrive at external device 116 after a deadline associated with the data. By way of example, but not limitation, the deadline associated with the data can be the latest acceptable time for the data to arrive at the external device 116. Any number of other deadlines or manners of specifying deadlines are possible.

Queue management component 204 can also include data forwarding component 216. The data forwarding component 204 can be configured to monitor the packet transmission queue shown as packet transmission queue 304 of FIG. 3 and, in response to a determination that a condition relative to the threshold associated with packet transmission queue 304 is satisfied, forward data from the data management queue 302 to packet transmission queue 304.

FIG. 3 illustrates a block diagram of a non-limiting medical device telemetry system 300 configured to facilitate management of transmission of data from an implantable device to an external device in accordance with descriptions of systems 100 and 200 described herein. Repetitive description of like elements employed in figures described herein is omitted for sake of brevity.

With reference to FIGS. 2 and 3, data for transmission 312 can be data from detection component 202 taken directly or derived from signal 222 that is for transmission to external device 116. Detection component 202 can supply the data for transmission 312 to data management queue 302 and/or to queue management component 204 for placement into data management queue 302. It is to be appreciated that, in various embodiments, there can be other intermediary components that move data between detection component 202 and queue management component 204.

While examples described depict a single data management queue 302 in an implantable device 104. It is to be appreciated that an implantable device 104 can employ a plurality of data management queues 302 that supply data to one or more packet transmission queues 304. In one example, there can be a data management queue 302 for each source of data, for each type of data, for each priority of data, or for each transmission destination of data, or any combinations thereof, or any other suitable criteria for establishing a data management queue 302. The number of data management queues 302 can be static, for example, established by a manufacturer, a user of, or an administrator (e.g., medical caregiver) of the implantable device 104 in some embodiments. In other embodiments, the number of data management queues 302 can be dynamic, for example, based on the number of sources of data, the number of types of data, the number of priorities of data, or the number of transmission destinations of data, or any other suitable criteria for establishing the number of data management queues 302.

Data management queue 302 can buffer $DATA_1$ 306a, $DATA_2$ 306b, $DATA_3$ 306c, $DATA_4$ 306d, . . . $DATA_M$ 306e (where M is an integer 0 or greater) from data for transmission 312 for forwarding to packet transmission queue 304. It is to be appreciated that $DATA_1$ 306a, $DATA_2$ 306b, $DATA_3$ 306c, $DATA_4$ 306d, . . . $DATA_M$ 306e can include various types of data, have different sizes, and have different formats. For example, $DATA_1$ 306a, $DATA_2$ 306b, $DATA_3$ 306c, $DATA_4$ 306d, . . . $DATA_M$ 306e can be segments of waveform data in some embodiments. In some embodiments, $DATA_1$ 306a, $DATA_2$ 306b, $DATA_3$ 306c, $DATA_4$ 306d can be segments of waveform data, while $DATA_M$ 306e can be associated marker data. In various embodiments, $DATA_1$ 306a, $DATA_2$ 306b, $DATA_3$ 306c, $DATA_4$ 306d, . . . $DATA_M$ 306e can be any suitable data for transmission from implantable device 104 to external device 116. $DATA_1$ 306a, $DATA_2$ 306b, $DATA_3$ 306c, $DATA_4$ 306d, . . . $DATA_M$ 306e can have or be associated with timestamps, $TS_1$, $TS_2$, $TS_3$, $TS_4$, . . . , $TS_M$, respectively.

In some embodiments, data in transit 308 can be a selection of data from data management queue 302 designated to be forwarded by data forwarding component 216 of FIG. 2 to packet transmission queue 304. Packet transmission queue 304 can buffer one or more packets of data (e.g., $PACKET_1$ 310a, $PACKET_2$ 310b, $PACKET_3$ 310c, $PACKET_4$ 310d, . . . $PACKET_N$ 310e, where N is an integer 0 or greater) for transmission to external device 116.

It is to be appreciated that in various embodiments, packet transmission queue 304 can be a conventional queue (e.g., BLE link layer) associated with a standard communication protocol (e.g., BLE), or a proprietary communication protocol while data management queue 302 can be an additional queue added outside of the standard communication protocol that can advantageously allow for avoiding or reducing the need to modify standard communication protocol components (e.g., BLE network stack layers) while achieving the benefits described herein. It is to be further appreciated that data forwarding component 216 can also supply data in transit 308 to communication component 218 for formatting and/or placement in packet transmission queue 304.

It is also to be appreciated that data forwarding component 216 and/or communication component 218 can employ commands and/or programs associated with standard communication protocol components (e.g., BLE network stack layers) or proprietary communication protocols to format and/or place data in transit 308 in packet transmission queue 304. In some embodiments, standard communication protocol components (e.g., BLE network stack layers) can manage transmission of one or more of packets of data $PACKET_1$ 310a, $PACKET_2$ 310b, $PACKET_3$ 310c, $PACKET_4$ 310d, . . . $PACKET_N$ 310e to external device 116.

In some embodiments, data forwarding component 216 is configured to determine if data management queue 302 contains data for transmission 312. If data management queue 302 contains data for transmission 312, data forwarding component 216 can monitor (e.g., poll, read memory locations associated with, make calls to components associated with) packet transmission queue 304 to determine a current size S (e.g., amount of packets, amount of data, or any other suitable measure of size) of packet transmission queue 304. Data forwarding component 216 can be configured to compare the size S of packet transmission queue 304 to a threshold size TH. If the size S of packet transmission queue 304 is determined to have a defined relationship to the threshold size TH (e.g., is determined to be less than or equal to TH, is determined to have an amount of packets or an amount of data within a range of TH (within 3 packets of TH), or any suitable function of TH), data forwarding component 216 can select one or more of $DATA_1$ 306a, $DATA_2$ 306b, $DATA_3$ 306c, $DATA_4$ 306d, . . . $DATA_M$ 306e from data management queue 302 for forwarding to packet transmission queue 304.

It is to be appreciated that the threshold size TH can be defined based on any number of sources and/or at any time (during use of the implantable device 104, prior to initial use of the implantable device 104 or the like). The threshold size can be defined based on programming the implantable device 104 with such information in some embodiments. In various embodiments, the threshold size can be defined by a manufacturer of implantable device 104, or by a user of or an administrator (e.g., medical caregiver) for implantable device 104 or dynamically determined by data forwarding component 216. As such, the threshold size defined can change from time to time and/or based on one or more different conditions.

In some embodiments, the threshold size TH is selected or determined to prevent packets of data from becoming stale while residing in packet transmission queue 304. For example, it can be known that for a particular communication protocol each packet typically takes an expected transmission time A milliseconds for transmission from packet transmission queue 304 under normal circumstances. Based upon knowledge of A and a typical deadline D for data to be transmitted from implantable device 104, and an estimate of the amount of time T to reach external device 116 once a packet is transmitted, a threshold size TH can be determined according to a function. By way of example, in a non-limiting embodiment, threshold size TH can be equal to (T–D)/A. It is to be appreciated that expected transmission time A can be determined (e.g., measured, calculated, estimated, inferred), for example, based on a real-time measurement of throughput using the particular communication protocol and/or communication network, a calculated function of a maximum throughput (e.g. theoretical or estimated) using the particular communication protocol and/or communication network, typical measured throughput determined via lab testing (e.g. under normal use or simulated varying use conditions), or any other suitable basis for determining expected transmission time A.

In another embodiment, where transmission of packets in inconsistent such as due to interference resulting in re-transmissions of packets, data forwarding component 216 can monitor respective times for each packet (or for one or more packets) to be transmitted from packet transmission queue 304 and dynamically adjust A continually or at regular intervals for a period of time (e.g., a fixed period, while A is outside of normal circumstances, or any other suitable period of time).

In another embodiment where deadlines are variable for different data in data management queue 302, data forwarding component 216 can dynamically adjust D continually or at regular intervals for a period of time based upon the deadlines $D_1$, $D_2$, $D_3$, $D_4$, . . . , $D_M$ of data in data management queue 302. It is to be appreciated that any suitable criteria for selecting or determining threshold size TH is encompassed herein.

Data forwarding component 216 can select one or more of $DATA_1$ 306a, $DATA_2$ 306b, $DATA_3$ 306c, $DATA_4$ 306d, . . . $DATA_M$ 306e from data management queue 302 for forwarding to packet transmission queue 304 according to any suitable characteristics of $DATA_1$ 306a, $DATA_2$ 306b, $DATA_3$ 306c, $DATA_4$ 306d, . . . $DATA_M$ 306e. For example, data management queue 302 can be a first in first out (FIFO) queue and data forwarding component 216 can select data in order from $DATA_1$ 306a, to $DATA_M$ 306e from data management queue 302 for forwarding to packet transmission queue 304. In another embodiment, data forwarding component 216 can employ respective deadlines and/or respective priorities (e.g., as discussed in more detail below) of $DATA_1$ 306a, $DATA_2$ 306b, $DATA_3$ 306c, $DATA_4$ 306d, . . . $DATA_M$ 306e for selection of one or more of $DATA_1$ 306a, $DATA_2$ 306b, $DATA_3$ 306c, $DATA_4$ 306d, . . . $DATA_M$ 306e from data management queue 302 for forwarding to packet transmission queue 304. It is to be appreciated that any suitable function of the characteristics of $DATA_1$ 306a, $DATA_2$ 306b, $DATA_3$ 306c, $DATA_4$ 306d, . . . $DATA_M$ 306e can be employed by data forwarding component 216 to select one or more of $DATA_1$ 306a, $DATA_2$ 306b, $DATA_3$ 306c, $DATA_4$ 306d, . . . $DATA_M$ 306e from data management queue 302 for forwarding to packet transmission queue 304.

Referring to FIGS. 2 and 3, packet arrival estimation component 212 can be configured to monitor data management queue 302 and determine respective estimated arrival times $E_1$, $E_2$, $E_3$, $E_4$, . . . , $E_M$ for $DATA_1$ 306a, $DATA_2$ 306b, $DATA_3$ 306c, $DATA_4$ 306d, . . . $DATA_M$ 306e in data management queue 302 to external device 116. It is to be appreciated that packet arrival estimation component 212 can update respective estimated arrival times $E_1$, $E_2$, $E_3$, $E_4$, . . . , $E_M$ continually, or at defined or dynamically determined intervals. In some embodiments where $DATA_1$ 306a, $DATA_2$ 306b, $DATA_3$ 306c, $DATA_4$ 306d, . . . $DATA_M$ 306e in data management queue 302 have the same deadlines and are ordered FIFO according to timestamp $TS_i$, where i is an integer from 1 to M, packet arrival estimation component 212 can determine an estimated arrival time $E_1$ for $DATA_1$ 306a to represent $E_2$, $E_3$, $E_4$, . . . , $E_M$, because if $DATA_1$ 306a is stale, then $DATA_2$ 306b, $DATA_3$ 306c, $DATA_4$ 306d, . . . $DATA_M$ 306e will also be stale.

Packet arrival estimation component 212 can estimate $E_1$, for example, based upon the size S of packet transmission queue 304. In a non-limiting embodiment, if size S is the amount of packets in packet transmission queue 304, then $E_1$ can equal the product of the size S multiplied by the typical amount of A milliseconds for transmission of a packet summed with the amount of time T to reach external device 116 once a packet is transmitted and the current time CT, $E_1=CT+(S*A)+T$.

In another embodiment, where $DATA_1$ 306a, $DATA_2$ 306b, $DATA_3$ 306c, $DATA_4$ 306d, . . . $DATA_M$ 306e have varied deadlines, packet arrival estimation component 212 can determine respective estimated arrival times $E_1$, $E_2$, $E_3$, $E_4$, . . . , $E_M$ for $DATA_1$ 306a, $DATA_2$ 306b, $DATA_3$ 306c, $DATA_4$ 306d, . . . $DATA_M$ 306e. In a non-limiting embodiment, if size S is the amount of packets in packet transmission queue 304 and $R_i$ is the number of data ahead of $DATA_i$ 306a data management queue 302, where i is an integer from 1 to M, then $E_i$ can equal the product of the sum of size S and $R_i$ multiplied by the typical amount of A milliseconds for transmission of a packet summed with the amount of time T to reach external device 116 once a packet is transmitted and the current time CT, $E_1=CT+((S+R_i)*A)+T$.

It is to be appreciated that estimated arrival time $E_i$ can be determined by packet arrival estimation component 212 using any suitable function. In some embodiments, A and T can be determined for each of (or, in some embodiments, one or more of) packets $PACKET_1$ 310a, $PACKET_2$ 310b, $PACKET_3$ 310c, $PACKET_4$ 310d, . . . $PACKET_N$ 310e and/or for each of $DATA_1$ 306a, $DATA_2$ 306b, $DATA_3$ 306c, $DATA_4$ 306d, . . . $DATA_M$ 306e, such as based on different sizes of data, different recipient external devices, or any other suitable criteria.

Data removal component 214 can be configured to monitor data management queue 302 and determine one or more of $DATA_1$ 306a, $DATA_2$ 306b, $DATA_3$ 306c, $DATA_4$ 306d, . . . $DATA_M$ 306e from data management queue 302 that is estimated to be stale when received by external device 116. For example, data removal component 214 can compare estimated arrival time $E_i$ with a latest arrival time $G_i$ at external device 116 for $DATA_i$. If $E_i$ is later than $G_i$, then data removal component 214 can remove $DATA_i$ from data management queue 302 to mitigate stale data from being transmitted to external device 116.

In a non-limiting embodiment, each (or, in some embodiments, one or more) of $DATA_1$ 306a, $DATA_2$ 306b, $DATA_3$ 306c, $DATA_4$ 306d, . . . $DATA_M$ 306e employ a common deadline D amount of time added to timestamp $TS_i$ in order to determine latest arrive time $G_i$ in which $DATA_i$ should arrive at external device 116, and be ordered FIFO according to $TS_i$. In this non-limiting embodiment, latest arrival time $G_i$ can be determined according to $G_i=TS_i+D$. However, $G_i$ can be determined according to any suitable function.

Given that $DATA_1$ 306a, $DATA_2$ 306b, $DATA_3$ 306c, $DATA_4$ 306d, . . . $DATA_M$ 306e can employ a common deadline D and are ordered FIFO by $TS_i$, $DATA_1$ 306a can act as a proxy for $DATA_2$ 306b, $DATA_3$ 306c, $DATA_4$ 306d, . . . $DATA_M$ 306e. If data removal component 214 determines that $E_1$ is later than $G_1$, data removal component 214 can remove $DATA_1$ 306a, $DATA_2$ 306b, $DATA_3$ 306c, $DATA_4$ 306d, . . . $DATA_M$ 306e from data management queue 302 as they will all have $E_i$ later than $G_i$.

Figure 4:
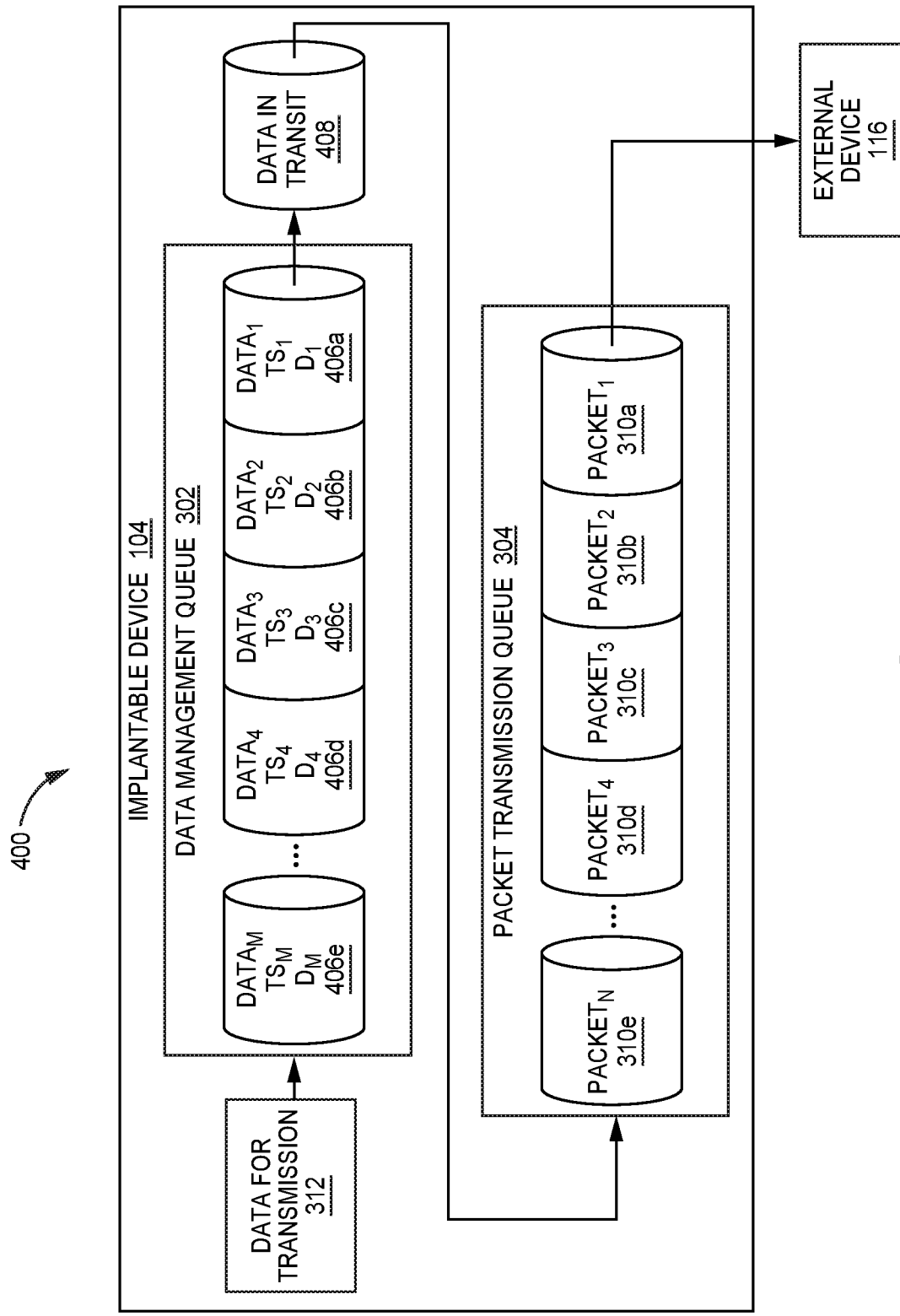
FIG. 4 illustrates a block diagram of an example, non-limiting medical device telemetry system facilitating management of transmission of data from an implantable device to an external device to mitigate transmission of stale data employing a data management queue with assigned deadlines for data in accordance with one or more embodiments described herein.

FIG. 4 illustrates a block diagram of a non-limiting medical device telemetry system 400 configured to facilitate management of transmission of data from an implantable device to an external device in accordance with descriptions of systems 100, 200, and 300 described herein. Repetitive description of like elements employed in figures described herein is omitted for sake of brevity. $DATA_1$ 506a, $DATA_2$ 506b, $DATA_5$ 506c, $DATA_4$ 506d, . . . $DATA_M$ 506e correspond to $DATA_1$ 306a, $DATA_2$ 306b, $DATA_3$ 306c, $DATA_4$ 306d, . . . $DATA_M$ 306e of FIG. 3 respectively adding deadlines $D_1$, $D_2$, $D_3$, $D_4$, . . . , $D_M$, which can have the same or different values.

In some embodiments, deadline component 206 can assign the same or different deadlines to different data based on any number of factors including, but not limited to, the type of data, the type of implantable device 104, the medical condition associated with the data, whether an emergency or non-emergency situation is detected with the patient associated with the implantable device 104, a status of the implantable device 104 (e.g., normal operation, abnormal operation, diagnostic operation, failure mode, alerting mode, low battery, or any other suitable status of the implantable device 104), the type of body in which the implantable device 104 is implanted, the type of external device 116 receiving the data, a type of environment in which external device 116 is located (e.g., physician's office, home, emergency room, operating room, ambulance, hospital, or any other suitable location), how the data will be used by external device 116 (e.g., presentation on a real-time display, storage in a patient record, triggering an alert, or any other suitable usage), a specification from external device 116, or any other suitable factors for assigning deadlines to data for transmission.

For example, an implantable device 104 for cardiac related functions can produce waveform data and marker data. Deadline component 206 can assign a first deadline to waveform data and a second deadline to marker data. In another non-limiting embodiment, an implantable device 104 that contains a variety of functions (e.g., cardiac, diabetic, oxygen, and any other suitable functions) can produce a variety of types of data, such as waveform, marker, blood-oxygen, pulse, blood pressure, and glucose data. Deadline component 206 can assign one or more of the types of data a different deadline. In another non-limiting embodiment, the same type of data can be assigned a different deadline based on the environment in which external device 116 that will receive the data is located. For example, blood-oxygen data being transmitted to external device 116 in a physician's office can be assigned a first deadline, while blood-oxygen data being transmitted to external device 116 in an emergency room can be assigned a second deadline. It is to be appreciated that deadline component 206 can assign deadlines to data using any suitable criteria and/or function.

Continuing with reference to FIG. 4, data removal component 214 is configured to monitor data management queue 302 and determine one or more of $DATA_1$ 406a, $DATA_2$ 406b, $DATA_3$ 406c, $DATA_4$ 406d, ... $DATA_M$ 406e from data management queue 302 that is estimated to be stale when received by external device 116. In some embodiments, each (or, in some embodiments, one or more) of $DATA_1$ 406a, $DATA_2$ 406b, $DATA_3$ 406c, $DATA_4$ 406d, ... $DATA_M$ 406e can have deadlines $D_1$, $D_2$, $D_3$, $D_4$, ..., $D_M$, respectively. In this non-limiting embodiment, latest arrival time $G_i$ can be determined according to $G_i = TS_i + D_i$. However, in other embodiments, $G_i$ can be determined according to any suitable function. If data removal component 214 determines that $E_i$ is later than $G_i$, data removal component 214 can remove $DATA_i$ from data management queue 302.

Data forwarding component 216 can select one or more of $DATA_1$ 406a, $DATA_2$ 406b, $DATA_3$ 406c, $DATA_4$ 406d, ... $DATA_M$ 406e from data management queue 302 for forwarding to packet transmission queue 304 according to any suitable characteristics of $DATA_1$ 406a, $DATA_2$ 406b, $DATA_3$ 406c, $DATA_4$ 406d, ... $DATA_M$ 406e. For example, data management queue 302 can be a FIFO queue and data forwarding component 216 can select data in order from $DATA_1$ 406a, to $DATA_M$ 406e from data management queue 302 for forwarding to packet transmission queue 304.

In some embodiments, data forwarding component 216 can employ a function of respective deadlines $D_1$, $D_2$, $D_3$, $D_4$, ..., $D_M$ for selection of one or more of $DATA_1$ 406a, $DATA_2$ 406b, $DATA_3$ 406c, $DATA_4$ 406d, ... $DATA_M$ 406e from data management queue 302 for forwarding to packet transmission queue 304. For example, data forwarding component 216 can select $DATA_i$ that has a smallest positive value of the result of the latest arrival time $G_i$ minus the expected arrival time $E_i$ for forwarding to packet transmission queue 304. It is to be appreciated that any suitable function of the characteristics of $DATA_1$ 406a, $DATA_2$ 406b, $DATA_3$ 406c, $DATA_4$ 406d, ... $DATA_M$ 406e can be employed to select one or more of $DATA_1$ 406a, $DATA_2$ 406b, $DATA_3$ 406c, $DATA_4$ 406d, ... $DATA_M$ 406e from data management queue 302 for forwarding to packet transmission queue 304.

Figure 5:
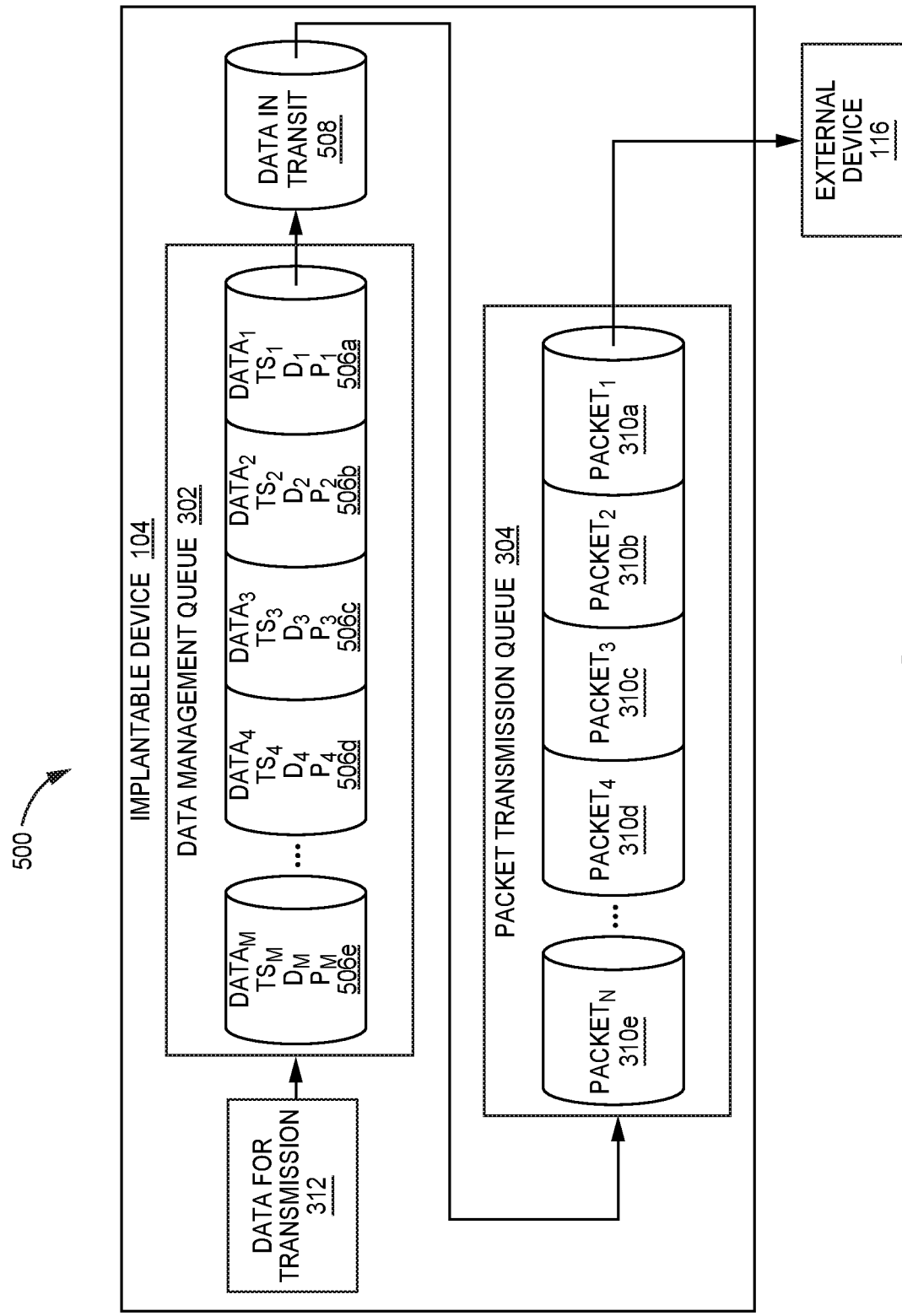
FIG. 5 illustrates a block diagram of an example, non-limiting medical device telemetry system facilitating management of transmission of data from an implantable device to an external device to mitigate transmission of stale data using a data management queue with assigned deadlines and priorities for data in accordance with one or more embodiments described herein.

FIG. 5 illustrates a block diagram of a non-limiting medical device telemetry system 500 configured to facilitate management of transmission of data from an implantable device to an external device in accordance with descriptions of systems 100, 200, 300, and 400 described herein. Repetitive description of like elements employed in figures described herein is omitted for sake of brevity. $DATA_1$ 506a, $DATA_2$ 506b, $DATA_3$ 506c, $DATA_4$ 506d, ... $DATA_M$ 506e correspond to $DATA_1$ 406a, $DATA_2$ 406b, $DATA_3$ 406c, $DATA_4$ 406d, ... $DATA_M$ 406e of FIG. 3 respectively adding priorities $P_1$, $P_2$, $P_3$, $P_4$, ..., $P_M$, which can have the same or different values. Priority component 208 can assign the same or different priorities to different types of data based on any number of factors including, but not limited to, the type of data, the type of implantable device 104, the medical condition associated with the data, whether an emergency or non-emergency situation is detected with the patient associated with the implantable device 104, a status of the implantable device 104 (e.g., normal operation, abnormal operation, diagnostic operation, failure mode, alerting mode, low battery, or any other suitable status of the implantable device 104), the type of body with which the implantable device 104 is associated, the type of external device 116 receiving the data, a type of environment in which external device 116 is located (e.g., physician's office, home, emergency room, operating room, ambulance, hospital, or any other suitable location), how the data will be used by external device 116 (e.g., presentation on a real-time display, storage in a patient record, triggering an alert, or any other suitable usage), a specification from external device 116, or any other suitable mechanism for assigning priorities to data. For example, an implantable device 104 for diabetic related functions can produce glucose data and insulin data. Priority component 208 can assign a first priority to glucose data and a second priority to insulin data.

In another non-limiting embodiment, an implantable device 104 that contains a variety of functions (e.g., cardiac, diabetic, oxygen, and any other suitable functions) can produce a variety of types of data, such as waveform, marker, blood-oxygen, pulse, blood pressure, and glucose data. Priority component 208 can assign one or more of the different types of data a different priority. In another non-limiting embodiment, the same type of data can be assigned a different priority based on the usage of the data in external device 116. For example, waveform data being transmitted to external device 116 for storage in a patient record can be assigned a first priority, while waveform data being transmitted to external device 116 during surgery can be assigned a second priority. It is to be appreciated that priority component 208 can assign priorities to data using any suitable criteria and/or function. It is to be appreciated that priorities $P_1$, $P_2$, $P_3$, $P_4$, ..., $P_M$ can be distinct from deadlines $D_1$, $D_2$, $D_3$, $D_4$, ..., $D_M$ and can employ different functions for determining their values. For example, the same type of data can have the same deadline but different priorities based on characteristics associated with the data. In some embodiments, the same type of data can have the same priority but different deadlines based on characteristics associated with the data. In another embodiment, the different types of data can have the same deadlines but different priorities based on characteristics associated with the data. In some embodiments, the different types of data can have the same priority but different deadlines based upon characteristics associated with the data.

Continuing with reference to FIG. 5, data forwarding component 216 can select one or more of $DATA_1$ 506a, $DATA_2$ 506b, $DATA_5$ 506c, $DATA_4$ 506d, . . . $DATA_M$ 506e from data management queue 302 for forwarding to packet transmission queue 304 according to any suitable characteristics of $DATA_1$ 506a, $DATA_2$ 506b, $DATA_5$ 506c, $DATA_4$ 506d, . . . $DATA_M$ 506e. For example, data management queue 302 can be a FIFO queue and data forwarding component 216 can select data in order from $DATA_1$ 506a, to $DATA_M$ 506e from data management queue 302 for forwarding to packet transmission queue 304.

In some embodiments, data forwarding component 216 can employ a function of respective deadlines $D_1$, $D_2$, $D_3$, $D_4$, . . . , $D_M$ and/or priorities $P_1$, $P_2$, $P_3$, $P_4$, . . . , $P_M$ for selection of one or more of $DATA_1$ 506a, $DATA_2$ 506b, $DATA_5$ 506c, $DATA_4$ 506d, . . . $DATA_M$ 506e from data management queue 302 for forwarding to packet transmission queue 304. For example, data forwarding component 216 can select $DATA_i$ that has a highest weight $W_i$ as function of $P_i$ and the result of $E_i$ minus $G_i$ for forwarding to packet transmission queue 304.

In a non-limiting embodiment, if two data have an equivalent smallest positive value result of $G_i$ minus $E_i$, then $DATA_i$ with a higher $P_i$ can be selected. In another non-limiting embodiment, if two data have an equivalent highest priority $P_i$, then $DATA_i$ with a smaller positive value result of $G_i$ minus $E_i$ can be selected. It is to be appreciated that any suitable function of the characteristics of $DATA_1$ 506a, $DATA_2$ 506b, $DATA_5$ 506c, $DATA_4$ 506d, . . . $DATA_M$ 506e can be employed to select one or more of $DATA_1$ 506a, $DATA_2$ 506b, $DATA_5$ 506c, $DATA_4$ 506d, . . . $DATA_M$ 506e from data management queue 302 for forwarding to packet transmission queue 304.

As noted with reference to FIG. 2, data throttling component 210 can be configured to monitor data management queue 302 to control throttling (e.g., adjust sampling rate of data, adjust channels of data, or adjust types of data) to increase or decrease data for transmission 312 for placement into data management queue 302 based upon throttling criteria. In some embodiments, data throttling component 210 can monitor a size Q of data management queue 302 and in response to throttling criteria such as the size Q of data management queue 302 exceeding a threshold queue size TQ, instruct (e.g., issue a signal to) detection component 202 to reduce an amount of data for transmission 312, such as by reducing a sampling rate of data, reducing channels of data, or reducing types of data being including in data for transmission 312.

In some embodiments, data throttling component 210 can monitor data being removed from data management queue 302 by data removal component 214 and identify throttling criteria such as characteristics of the removed data (e.g., type of data, source of data, size of data, or any other suitable characteristics the data). In some embodiments, data throttling component 210 can perform the identification on a continual basis or when an amount of data being removed exceeds one or more removal thresholds.

Data throttling component 210 can instruct detection component 202 to reduce an amount of data for transmission 312 based upon the identified characteristics, such as by reducing a sampling rate of data with the identified characteristics, reducing channels of data associated with the identified characteristics, or reducing data with the identified characteristics from being including in data for transmission 312. For example, if a particular type of data is being removed, then data throttling component 210 can instruct detection component 202 to reduce a sampling rate of the type of data, reducing one or more channels associated with the type of data, or stop including the type of data in the data for transmission 312. It is to be appreciated that data throttling component 210 can also increase data for transmission 312, for example, if conditions that initiated a reduction of data for transmission 312 no longer exist.

Figure 6:
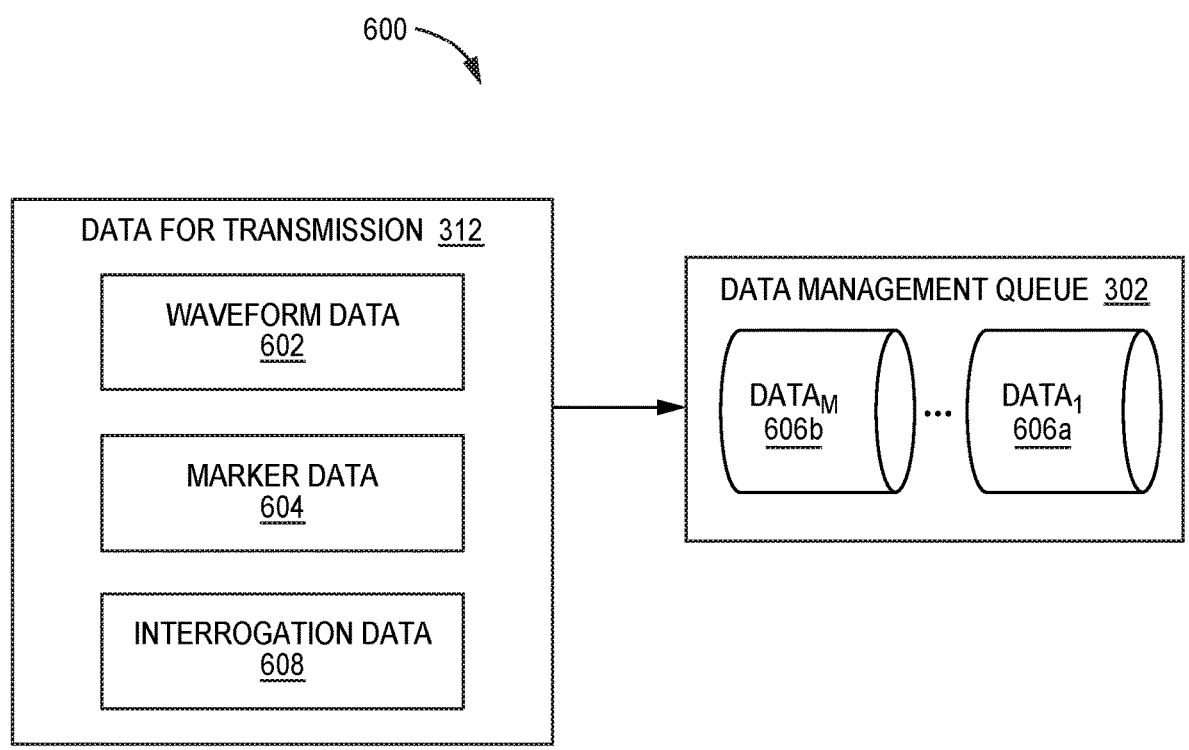
FIG. 6 illustrates a block diagram of an example, non-limiting medical device telemetry system facilitating management of transmission of waveform data and marker data from an implantable device to an external device to mitigate transmission of stale data using a data management queue in accordance with one or more embodiments described herein.

FIG. 6 illustrates a block diagram of a non-limiting medical device telemetry system 600 configured to facilitate management of transmission of data from an implantable device to an external device in accordance with descriptions of systems 100, 200, 300, 400, and 500 described herein. Repetitive description of like elements employed in figures described herein is omitted for sake of brevity. $DATA_1$ 606a, . . . $DATA_M$ 606e correspond to $DATA_1$ 506a, . . . $DATA_M$ 506e, or $DATA_1$ 406a, . . . $DATA_M$ 406e, or $DATA_1$ 306a, . . . $DATA_M$ 306e. In this embodiment, data for transmission 312 includes waveform data 602, marker data 604, and interrogation data 608 (e.g., associated with a cardiac implantable device). In a non-limiting embodiment, if data throttling component 210 determines that one or more of waveform data 602, marker data 604 or interrogation data 608 are being removed by data removal component 214, data throttling component 210 can instruct detection component 202 to eliminate one or more of waveform data 602, marker data 604, or interrogation data 608 from the data for transmission 312, or reduce a sampling rate of waveform data 602 and/or marker data 604.

Figure 7:
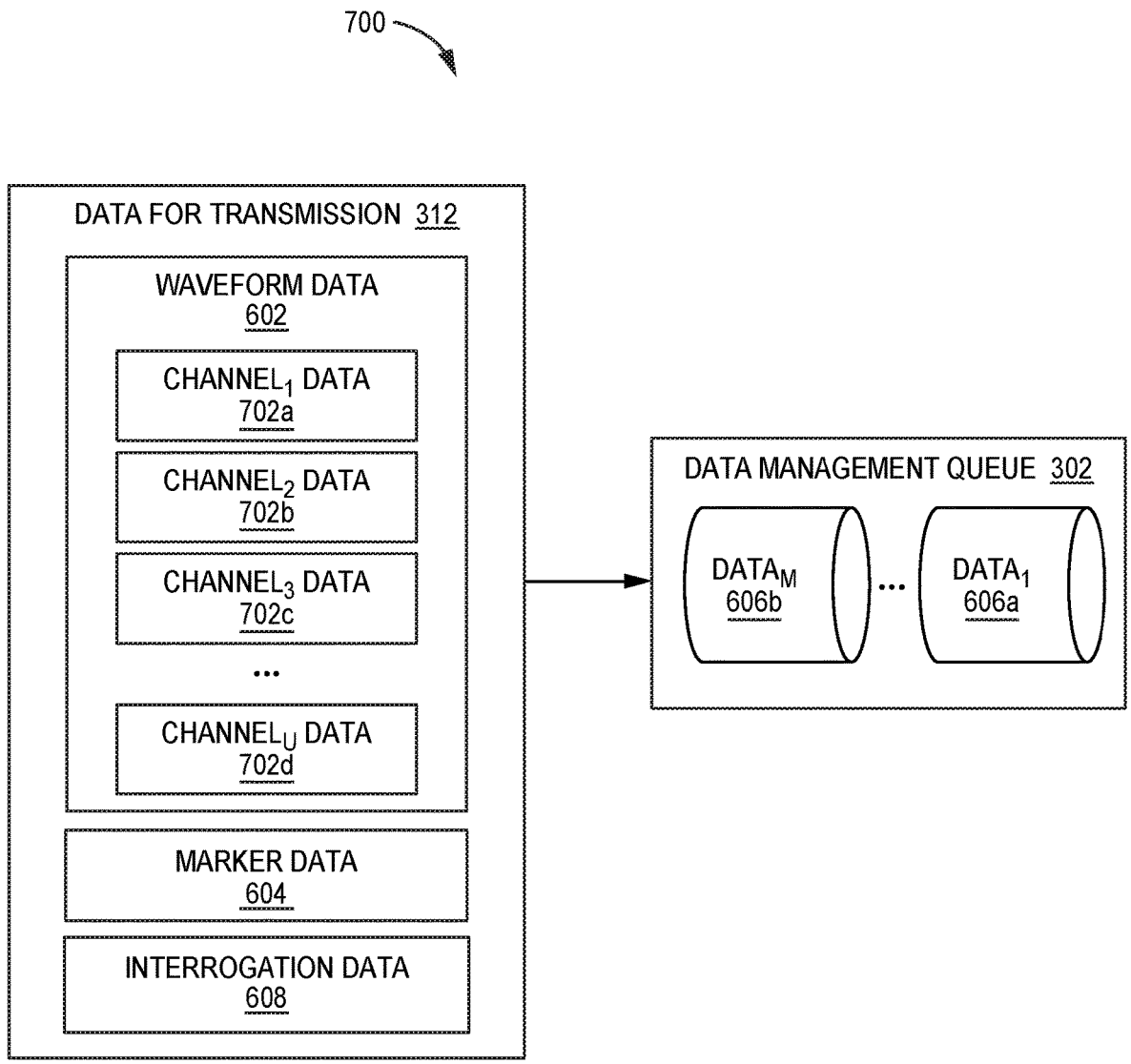
FIG. 7 illustrates a block diagram of an example, non-limiting medical device telemetry system facilitating management of transmission of marker data and waveform data including channel data from an implantable device to an external device to mitigate transmission of stale data employing a data management queue in accordance with one or more embodiments described herein.

FIG. 7 illustrates a block diagram of a non-limiting medical device telemetry system 700 configured to facilitate management of transmission of data (e.g., real-time data and/or stored data) from an implantable device to an external device in accordance with descriptions of systems 100, 200, 300, 400, 500, and 600 described herein. Repetitive description of like elements employed in figures described herein is omitted for sake of brevity. In this embodiment, data for transmission 312 includes waveform data 602, marker data 604, and interrogation data 608 (e.g., associated with a cardiac implantable device).

Waveform data 602 can include channel data $CHANNEL_1DATA$ 702a, $CHANNEL_2DATA$ 702b, $CHANNEL_3DATA$ 702c, . . . $CHANNEL_UDATA$ 702d, where U is a positive integer. In a non-limiting embodiment, if data throttling component 210 determines that one or more of waveform data 602, marker data 604 or interrogation data 608 are being removed by data removal component 214, data throttling component 210 can instruct detection component 202 to eliminate one or more of waveform data 602, $CHANNEL_1DATA$ 702a, $CHANNEL_2DATA$ 702b, $CHANNEL_3DATA$ 702c, . . . $CHANNEL_UDATA$ 702d, interrogation data 608, or marker data 604 from the data for transmission 312, or reduce a sampling rate of waveform data 602, $CHANNEL_1DATA$ 702a, $CHANNEL_2DATA$ 702b, $CHANNEL_3DATA$ 702c, . . . $CHANNEL_UDATA$ 702d, marker data 604 and/or interrogation data 608.

Figure 8:
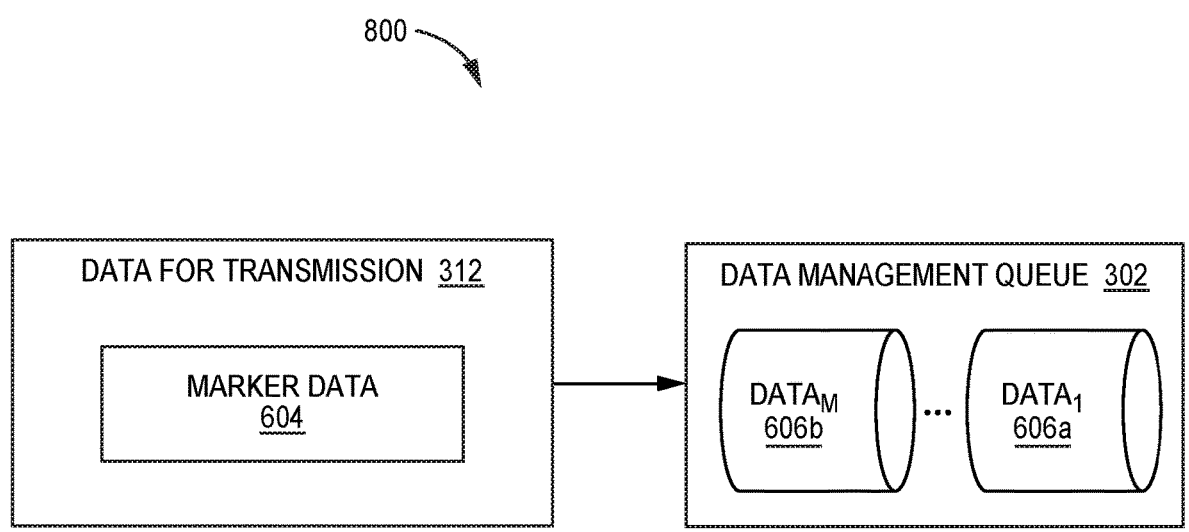
FIG. 8 illustrates a block diagram of an example, non-limiting medical device telemetry system facilitating management of transmission of marker data from an implantable device to an external device to mitigate transmission of stale data employing a data management queue in accordance with one or more embodiments described herein.

FIG. 8 illustrates a block diagram of a non-limiting medical device telemetry system 800 configured to facilitate management of transmission of data (e.g., sensed data and/or stored data) from an implantable device to an external device in accordance with descriptions of systems 100, 200, 300, 400, 500, 600, 700 described herein. In this embodiment, data for transmission 312 includes waveform data 602, interrogation data 608, and marker data 604 (e.g., associated with a cardiac implantable device). In this embodiment, data for transmission 312 is depicted in which data throttling component 210 has instructed detection component 202 to eliminate waveform data 602 and interrogation data 608 in favor of supplying marker data 604 in the data for transmission 312.

FIGS. 9-14 illustrate flow diagrams of example, non-limiting methods facilitating mitigation of transmission of stale data in accordance with one or more embodiments described herein. In some embodiments, the methods can facilitate management of transmission of data from an implantable device (e.g., implantable device 104) to an external device (e.g., external device 116) in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 9:
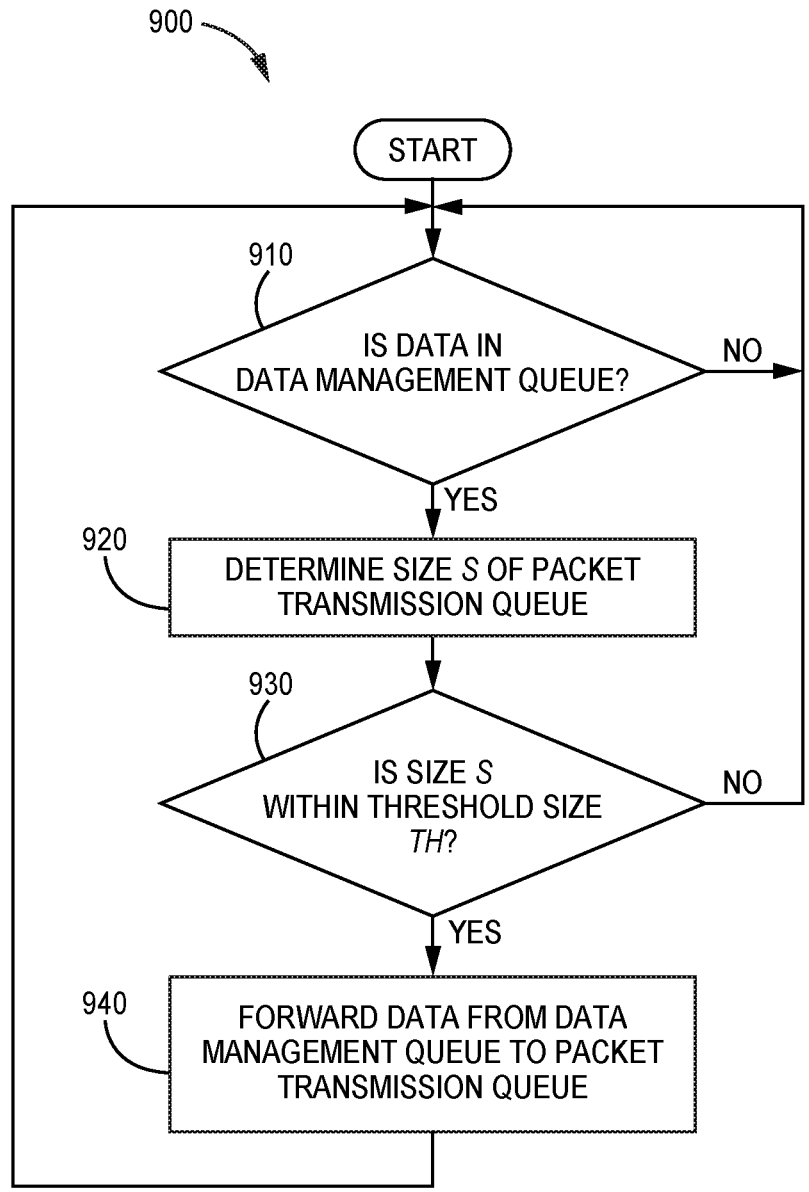
FIG. 9 illustrates a flow diagram of an example, non-limiting method of facilitating monitoring a packet transmission queue to mitigate transmission of stale data in accordance with one or more embodiments described herein.

Referring now to FIG. 9, shown is a flow diagram of an example method 900 configured to monitor a packet transmission queue 304 and, based on a threshold associated with the packet transmission queue 304 being satisfied, forward data from a data management queue 302 to the packet transmission queue 304 by an implantable device in accordance with one embodiment. At 910, a determination is made whether there is data for transmission in data management queue 302 (e.g., by a data forwarding component 216, a queue management component 204, or an implantable device 104). If a determination has been made that there is no data for transmission in data management queue 302, the method proceeds to 910. If a determination has been made that there is data for transmission in data management queue 302, the method proceeds to 920. At 920, a size of packet transmission queue 304 is determined (e.g., by a data forwarding component 216, a queue management component 204, or an implantable device 104). At 930, a determination is made whether the size of packet transmission queue 304 is within threshold size TH (e.g., by a data forwarding component 216, a queue management component 204, or an implantable device 104). If a determination has been made that the size of packet transmission queue 304 is not within threshold size TH, the method proceeds to 910. If a determination has been made that the size of packet transmission queue 304 is within threshold size TH, the method proceeds to 940. At 940, some data from data management queue 302 is forwarded to packet transmission queue 304 (e.g., by a data forwarding component 216, a queue management component 204, or an implantable device 104). The method can optionally proceed to 910. For example, the method may not proceed to 910 if the implantable device is no longer in communication with external device 116.

Figure 10:
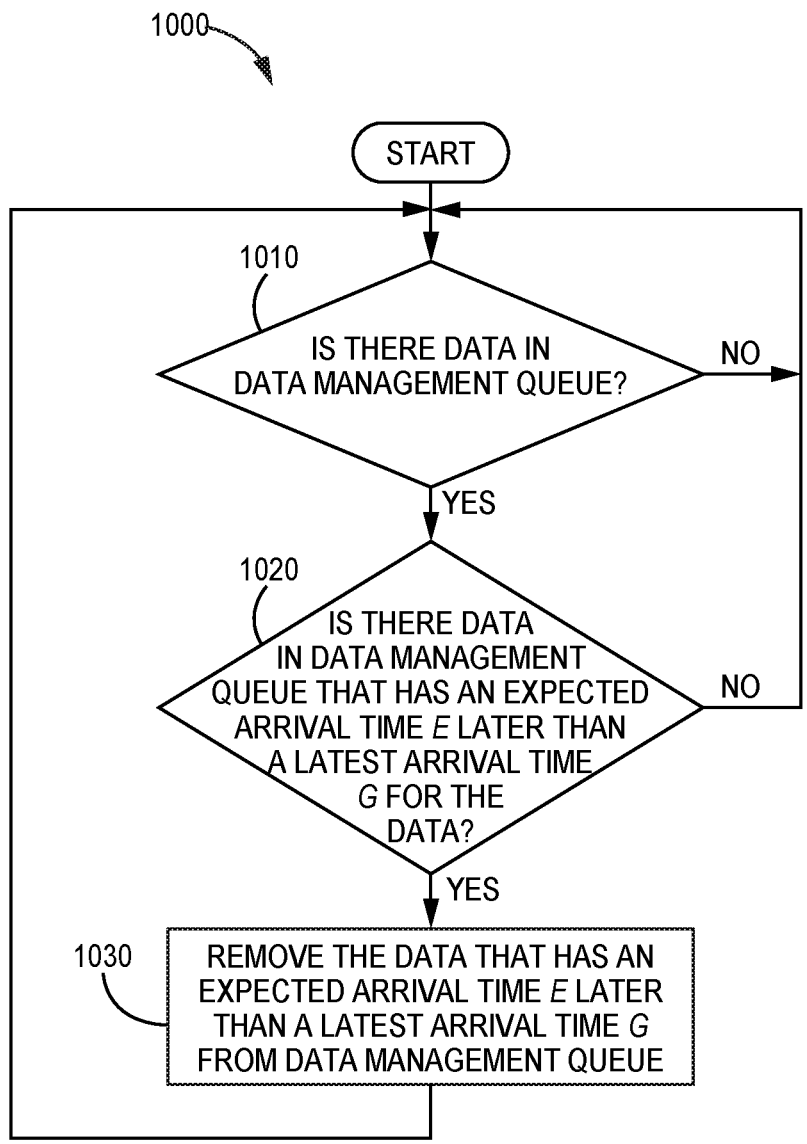
FIG. 10 illustrates a flow diagram of an example, non-limiting method of facilitating removing stale data from a data management queue by an implantable device to mitigate transmission of stale data in accordance with one or more embodiments described herein.

Referring now to FIG. 10, shown is a flow diagram of an example method 1000 configured to remove stale data from data management queue 302 by an implantable device in accordance with one embodiment. At 1010, a determination is made whether there is data for transmission in data management queue 302 (e.g., by a data removal component 214, a queue management component 204, or an implantable device 104). If a determination has been made that there is no data for transmission in data management queue 302, the method proceeds to 1010. If a determination has been made that there is data for transmission in data management queue 302, the method proceeds to 1020. At 1020, a determination is made whether there is data in data management queue 302 that has an expected arrival time E later than a latest arrival time G for the data (e.g., by a data removal component 214, a queue management component 204, or an implantable device 104). If a determination has been made that there is no data in data management queue 302 that has an expected arrival time E later than a latest arrival time G for the data, the method proceeds to 1010. If a determination has been made that there is data in data management queue 302 that has an expected arrival time E later than a latest arrival time G for the data, the method proceeds to 1030. At 1030, the data in data management queue 302 that has an expected arrival time E later than a latest arrival time G is removed from data management queue 302 (e.g., by a data removal component 214, a queue management component 204, or an implantable device 104). The method can optionally proceed to 1010. For example, the method may not proceed to 1010 if the implantable device is no longer in communication with external device 116.

Figure 11:
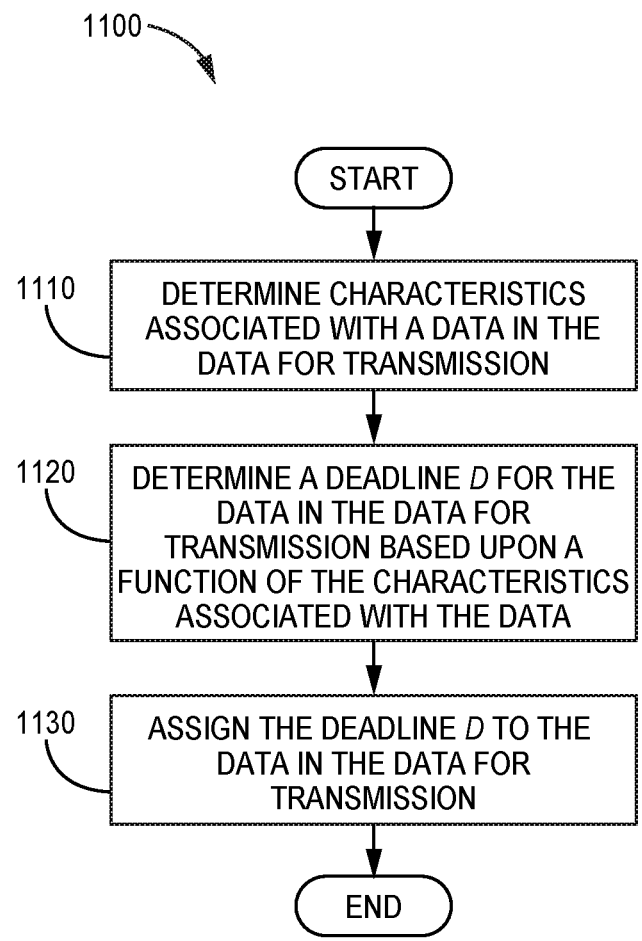
FIG. 11 illustrates a flow diagram of an example, non-limiting method of facilitating assigning deadlines to data for transmission by an implantable device to mitigate transmission of stale data in accordance with one or more embodiments described herein.

Referring now to FIG. 11, shown is a flow diagram of an example method 1100 configured to assign deadlines to data in the data for transmission 312 by an implantable device in accordance with one embodiment. At 1110, characteristics associated with data in the data for transmission 312 are determined (e.g., by a deadline component 206, a queue management component 204, or an implantable device 104). At 1120, a deadline D is determined for the data in the data for transmission 312 based on the characteristics associated with the data (e.g., by a deadline component 206, a queue management component 204, or an implantable device 104). At 1130, the deadline D is assigned to the data in the data for transmission 312 (e.g., by a deadline component 206, a queue management component 204, or an implantable device 104).

Figure 12:
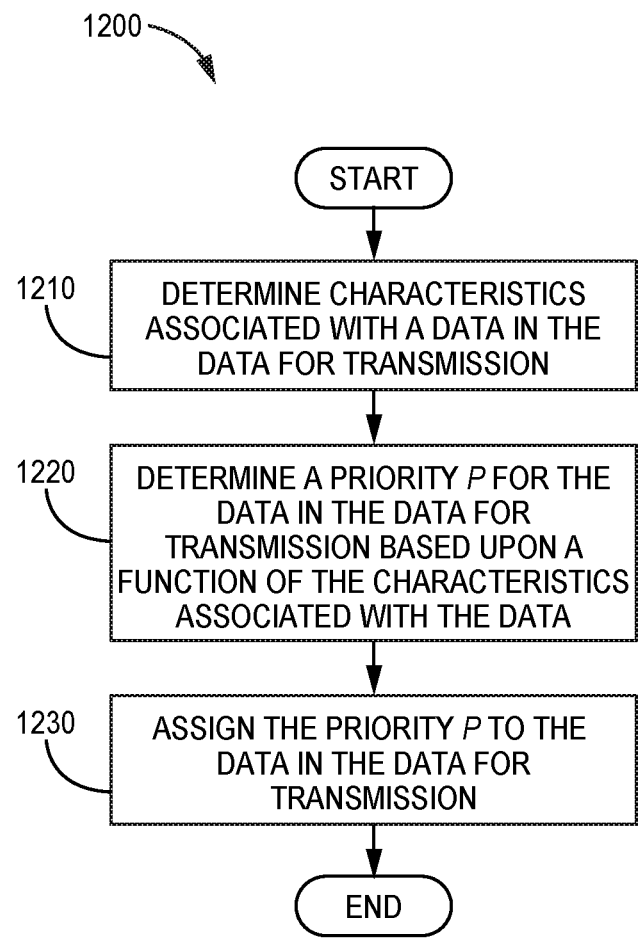
FIG. 12 illustrates a flow diagram of an example, non-limiting method of facilitating assignment of priorities to data for transmission by an implantable device to mitigate transmission of stale data in accordance with one or more embodiments described herein.

Referring now to FIG. 12, shown is a flow diagram of an example method 1100 configured to assign priorities to data in the data for transmission 312 by an implantable device in accordance with one embodiment. At 1210, characteristics associated with a data in the data for transmission 312 are determined (e.g., by a priority component 208, a queue management component 204, or an implantable device 104). At 1220, a priority P is determined for the data in the data for transmission 312 based upon the characteristics associated with the data (e.g., by a priority component 208, a queue management component 204, or an implantable device 104). At 1230, the priority P is assigned to the data in the data for transmission 312 (e.g., by a priority component 208, a queue management component 204, or an implantable device 104).

Figure 13:
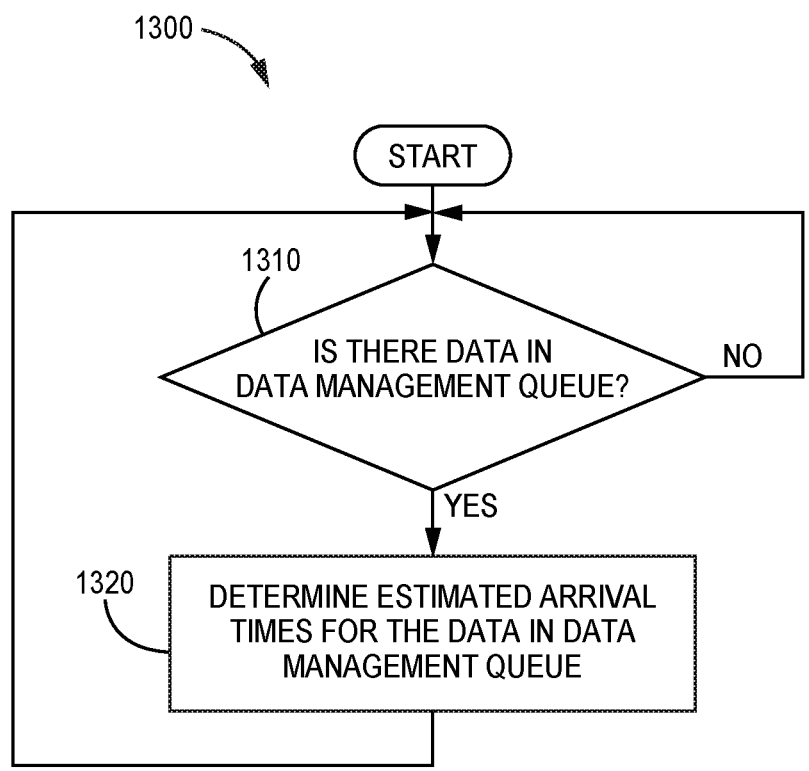
FIG. 13 illustrates a flow diagram of an example, non-limiting method of facilitating determining estimated arrival times for data in a data management queue by an implantable device to mitigate transmission of stale data in accordance with one or more embodiments described herein.

Referring now to FIG. 13, shown is a flow diagram of an example method 1300 configured to determine estimated arrival times for data in data management queue 302 by an implantable device in accordance with one embodiment. At 1310, a determination is made whether there is data for transmission in data management queue 302 (e.g., by a packet arrival estimation component 212, a queue management component 204, or an implantable device 104). If a determination has been made that there is no data for transmission in data management queue 302, the method proceeds to 1310. If a determination has been made that there is data for transmission in data management queue 302, the method proceeds to 1320. At 1320, estimated arrival times E for the data in data management queue 302 is determined (e.g., by a packet arrival estimation component 212, a queue management component 204, or an implantable device 104). The method can optionally proceed to 1310. For example, the method may not proceed to 1310 if the implantable device is no longer in communication with external device 116.

Figure 14:
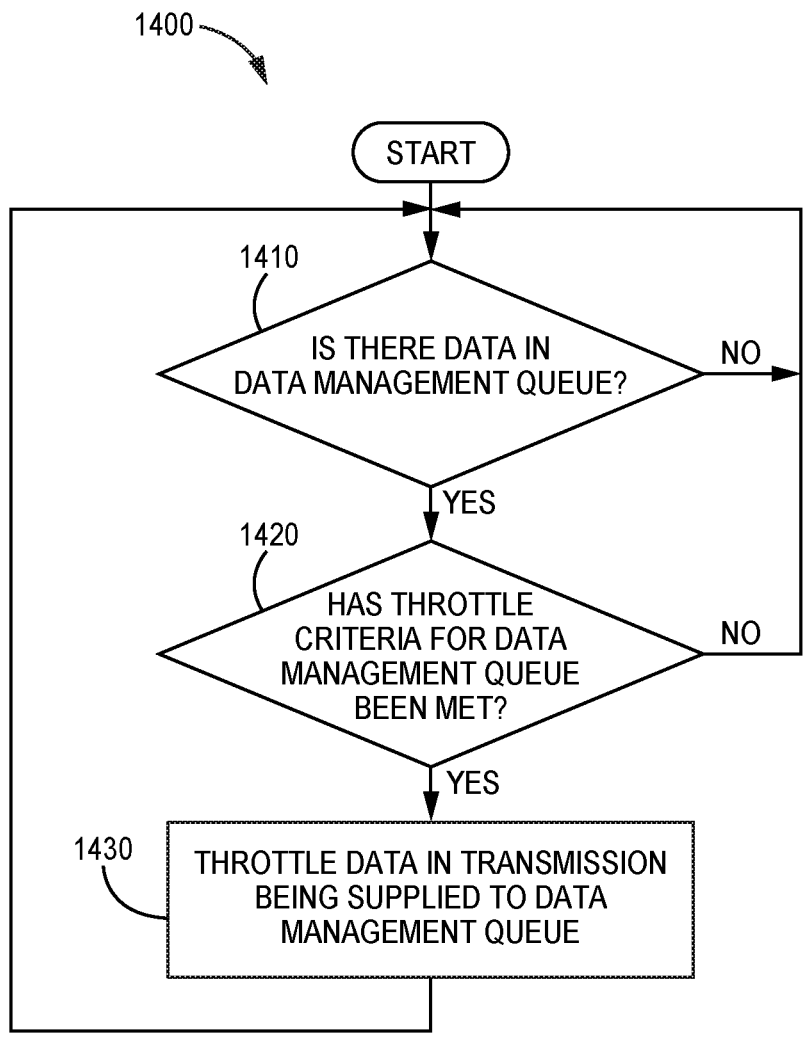
FIG. 14 illustrates a flow diagram of an example, non-limiting method of facilitating throttling data for transmission by an implantable device to mitigate transmission of stale data in accordance with one or more embodiments described herein.

Referring now to FIG. 14, shown is a flow diagram of an example method 1400 configured to throttle data for transmission 312 by an implantable device in accordance with one embodiment. At 1410, a determination is made whether there is data for transmission in data management queue 302 (e.g., by a data throttling component 210, a queue management component 204, or an implantable device 104). If a determination has been made that there is no data for transmission in data management queue 302, the method proceeds to 1410. If a determination has been made that there is data for transmission in data management queue 302, the method proceeds to 1420. At 1420, a determination is made whether throttling criteria for data management queue 302 has been met (e.g., by a data throttling component 210, a queue management component 204, or an implantable device 104). If a determination has been made that throttling criteria for data management queue 302 has not been met, the method proceeds to 1410. If a determination has been made that throttling criteria for data management queue 302 has been met, the method proceeds to 1430. At 1430, data in transmission being supplied to data management queue 302 is throttled, such as, in a non-limiting embodiment, based on a function of the throttling criteria (e.g., by a detection component 202, a data throttling component 210, a queue management component 204, or an implantable device 104). The method can optionally proceed to 1410. For example, the method may not proceed to 1410 if the implantable device is no longer in communication with external device 116.

Figure 15:
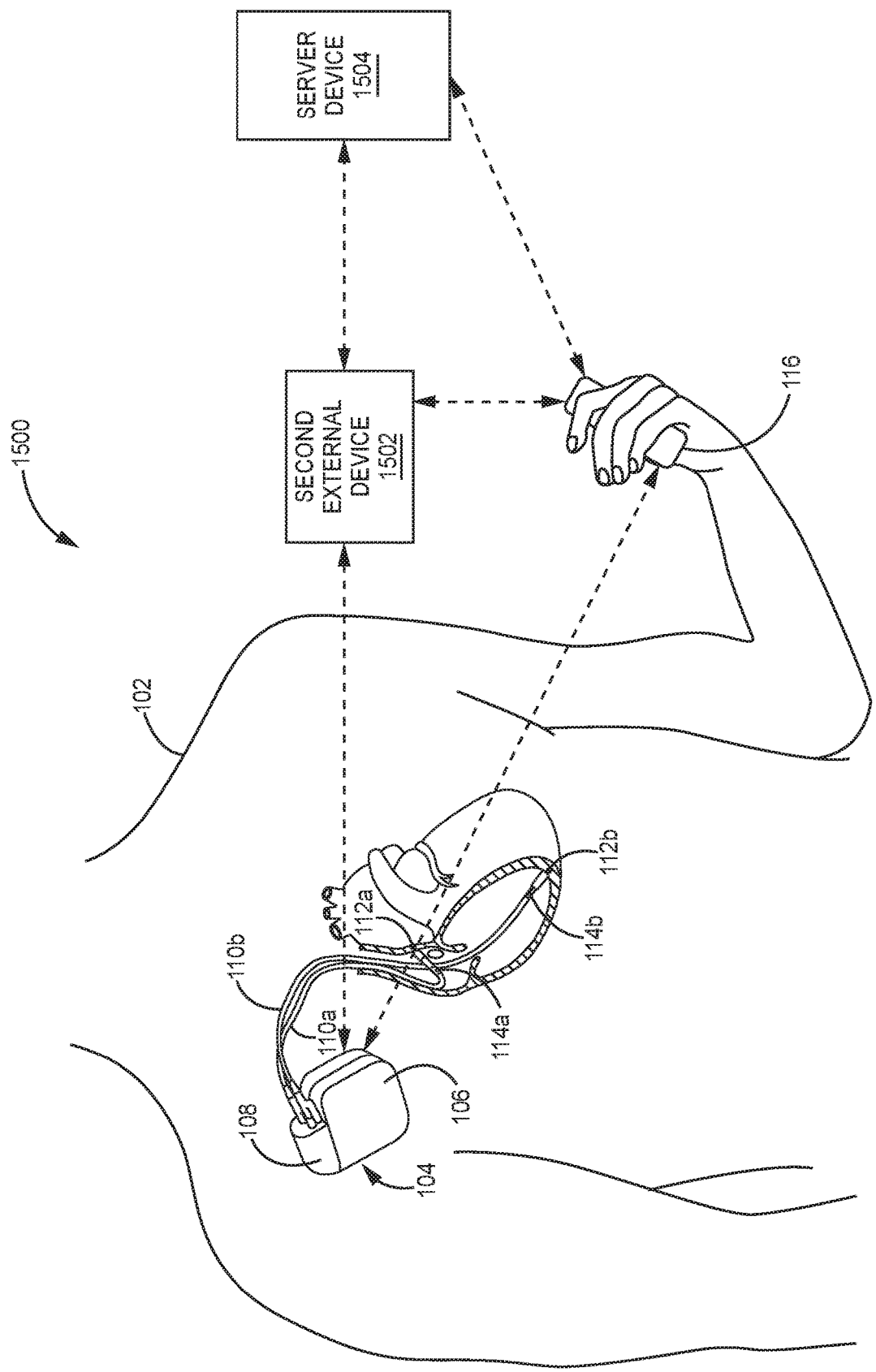
FIG. 15 illustrates a block diagram of an example, non-limiting medical telemetry system facilitating management of transmission of data by an implantable device to a first external device and a second external device to mitigate transmission of stale data in accordance with one or more embodiments described herein.

FIG. 15 illustrates a block diagram of an example, non-limiting medical telemetry system facilitating management of data by an implantable device to a first external device and a second external device to mitigate transmission of stale data in accordance with one or more embodiments described herein. Although not shown, as with system 100, it is to be appreciated that the implantable device 104 is implanted within (or provided on) a body of a living being. For exemplary purposes, system 1500 is described with the assumption that the implantable device 104 is implanted within (or provided on) a human being. In some embodiments, the implantable device 104 can be implanted within (or provided on) an animal.

System 1500 includes one or more of the structure, features and/or functionality of components of FIGS. 1-8 with the addition of various components included in the respective devices of system 1500 that facilitate the various implementations of system 1500. In accordance with system 1500, external device 116 and implantable device 104 can include one or more of the same or similar components, structure, features and/or functionality as previously described with respect to FIGS. 1-8. Second external device 1502 can include one or more of the structure, features and functionalities of external device 116. Repetitive description of like elements employed in other embodiments described herein is omitted for sake of brevity.

In some embodiments, implantable device 104 can transmit (e.g., concurrently or during non-overlapping time periods) data to both external device 116 and second external device 1502. Furthermore, implantable device 104 can employ distinctive criteria or mechanisms to throttle or assign various deadlines and priorities to respective data for transmission to external device 116 and second external device 1502 based upon respective characteristics (e.g., the type of external device 116, a type of environment in which external device 116 is located (e.g., physician's office, home, emergency room, operating room, ambulance, hospital, or any other suitable location), a specification from external device 116) of external device 116 and second external device 1502. Implantable device 104 can also employ distinctive criteria or mechanisms for removing respective data for transmission to external device 116 and second external device 1502 from data management queue 302 or forwarding respective data for transmission to external device 116 and second external device 1502 to packet transmission queue 304.

In addition, external device 116 and/or second external device 1502 can communicate all or a portion of data received from implantable device 104 directly or after transformation to server device 1504 for further processing or storage. It is to be appreciated that external device 116 and/or second external device 1502 can be an access point that relays data received from implantable device 104 to server device 1504. For example, in a situation in which remote evaluation of a patient is required, external device 116 can function as an access point that relays data received from implantable device 104 to server device 1504 located at a remote location from body 102 (e.g., patient is at home and doctor is at hospital, patient is in physician's office and need specialist consult from a different physician's office, or any other suitable situation where body 102 is physically remote from server device 1504).

Figure 16:
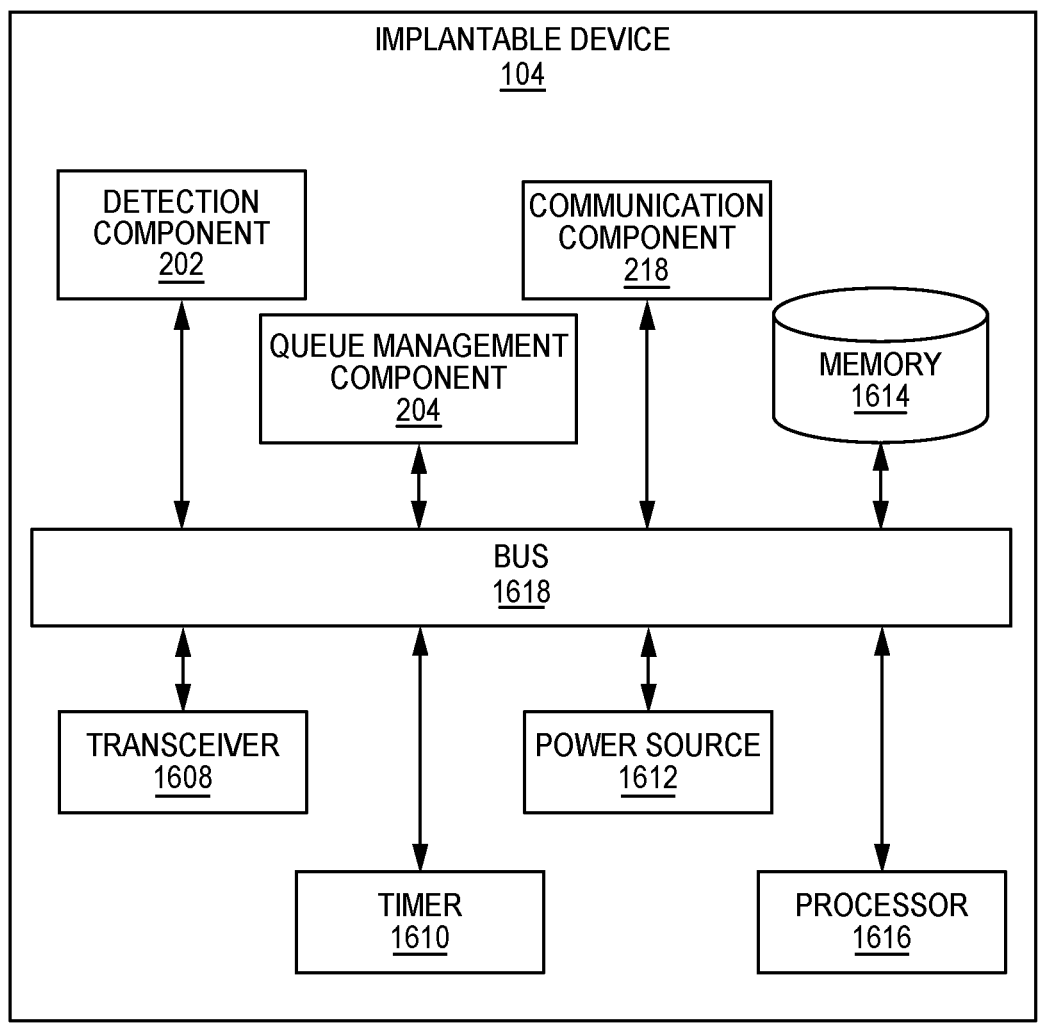
FIG. 16 illustrates a block diagram of an example, non-limiting implantable device configured to mitigate transmission of stale data in accordance with one or more embodiments described herein.

FIG. 16 illustrates a block diagram of an example, non-limiting implantable device configured to mitigate transmission of stale data in accordance with one or more embodiments described herein. The implantable device 104 includes detection component 202, queue management component 204, and communication component 218. Implantable device 104 also includes a transceiver 1608, a timer 1610 and a power source 1612. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

Implantable device 104 can include memory 1614 for storing computer executable components and instructions. Implantable device 104 can further include a processor 1616 to facilitate operation of the instructions (e.g., computer executable components and instructions) by implantable device 104. Implantable device 104 can include a bus 1618 that couples the various components of the implantable device 104, including, but not limited to, detection component 202, queue management component 204, communication component 218, transceiver 1608, timer 1610, power source 1612, processor 1616 and/or memory 1614. Repetitive description of like elements employed in other examples described herein is omitted for sake of brevity.

Figure 17:
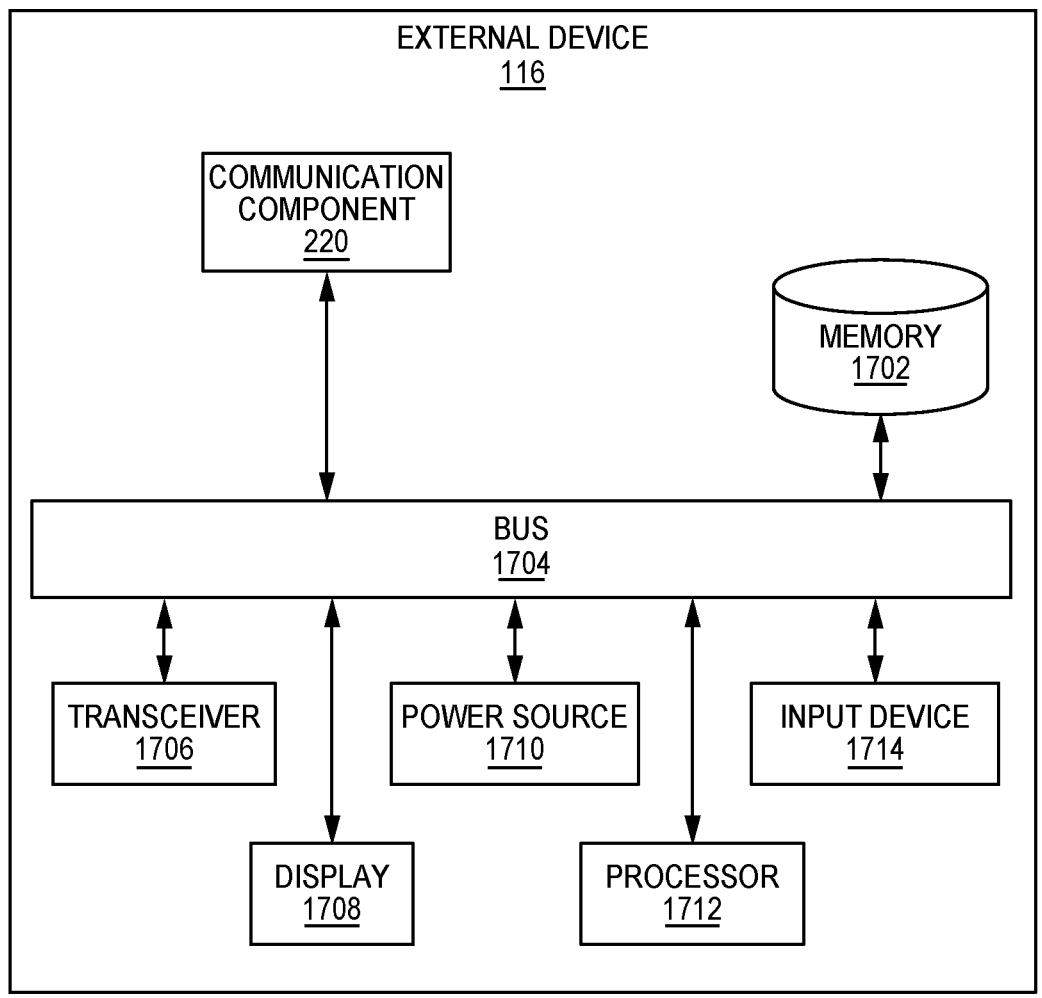
FIG. 17 illustrates a block diagram of an example, non-limiting external device in accordance with one or more embodiments described herein.

FIG. 17 illustrates a block diagram of an example, non-limiting external device (e.g., external device 116) in accordance with one or more examples described herein. External device 116 includes communication component 220. External device 116 also includes a transceiver 1706, a display 1708, a power source 1412, and an input device 1714. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

External device 116 can include memory 1702 for storing computer executable components and instructions. External device 116 can further include a processor 1712 to facilitate operation of the instructions (e.g., computer executable components and instructions) by external device 116. External device 116 can include a bus 1704 that couples the various components of the implantable device 104, including, but not limited to, communication component 220, transceiver 1706, display 1708, power source 1712, input device 1714, processor 1712 and/or memory 1702. Repetitive description of like elements employed in other figures described herein is omitted for sake of brevity.

Figure 18:
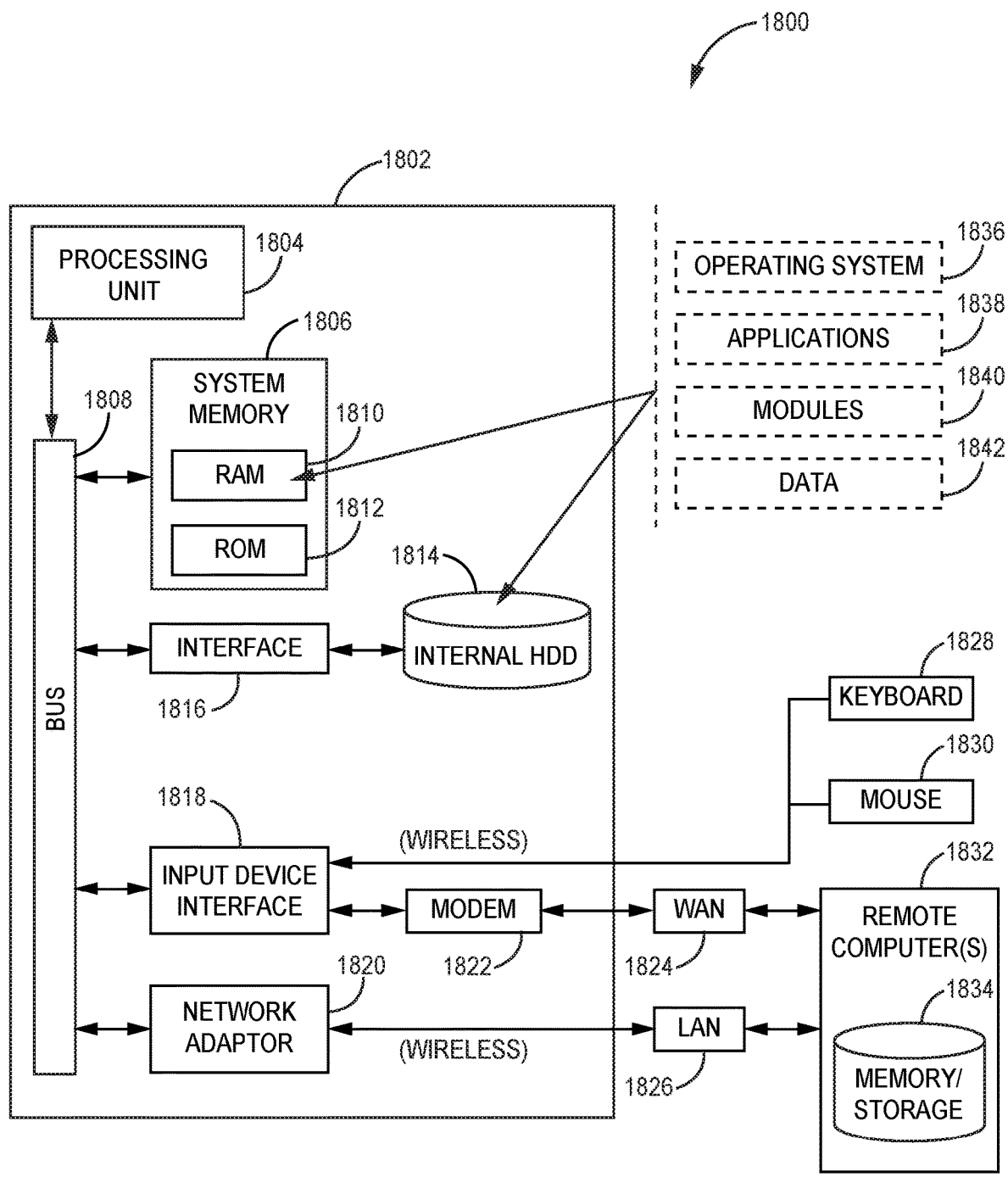
FIG. 18 illustrates a block diagram of a computer operable to facilitate telemetry with or via an implantable device to mitigate transmission of stale data in accordance with one or more embodiments described herein.

FIG. 18 illustrates a block diagram of a computer operable to facilitate telemetry with or via an implantable device to mitigate transmission of stale data in accordance with one or more embodiments described herein. For example, in some embodiments, the computer can be or be included within implantable device 104, external device 116 and/or server device 1404. Repetitive description of like elements employed in figures described herein is omitted for sake of brevity.

In order to provide additional context for one or more embodiments described herein, FIG. 18 and the following discussion are intended to provide a brief, general description of a suitable computing environment 1800 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, example environment 1800 that can be employed to implement one or more embodiments of the embodiments described herein includes computer 1802. Computer 1802 includes processing unit 1804, system memory 1806 and system bus 1808. System bus 1808 couples system components including, but not limited to, system memory 1806 to processing unit 1804. Processing unit 1804 can be any of various commercially available processors. Dual microprocessors and other multi processor architectures can also be employed as processing unit 1804.

System bus 1808 can be any of several types of bus structure that can further interconnect to a memory bus (with or without a memory controller), a peripheral bus, and a local bus using any of a variety of commercially available bus architectures. System memory 1806 includes RAM 1810 and ROM 1812. A basic input/output system (BIOS) can be stored in a non-volatile memory such as ROM, erasable programmable read only memory (EPROM), EEPROM, which BIOS contains the basic routines that help to transfer information between elements within computer 1802, such as during startup. RAM 1810 can also include a high-speed RAM such as static RAM for caching data.

Computer 1802 further includes internal hard disk drive (HDD) 1814 (e.g., Enhanced Integrated Drive Electronics (EIDE), Serial Advanced Technology Attachment (SATA)). HDD 1814 can be connected to system bus 1808 by hard disk drive interface 1816. The drives and their associated computer-readable storage media provide nonvolatile storage of data, data structures, computer-executable instructions, and so forth. For computer 1802, the drives and storage media accommodate the storage of any data in a suitable digital format.

A number of program modules can be stored in the drives and RAM 1810, including operating system 1836, one or more application programs 1838, other program modules 1840 and program data 1842. All or portions of the operating system, applications, modules, and/or data can also be cached in RAM 1810. The systems and methods described herein can be implemented utilizing various commercially available operating systems or combinations of operating systems.

A mobile device can enter commands and information into computer 1802 through one or more wireless input devices, e.g., wireless keyboard 1828 and a pointing device, such as wireless mouse 1830. Other input devices (not shown) can include a smart phone, tablet, laptop, wand, wearable device or the like. These and other input devices are often connected to the processing unit 1804 through input device interface 1818 that can be coupled to system bus 1808, but can be connected by other interfaces, such as a parallel port, an IEEE serial port, a game port and/or a universal serial bus (USB) port.

Computer 1802 can operate in a networked environment using logical connections via wired and/or wireless communications to one or more remote computers, such as remote computer(s) 1832. Remote computer(s) 1832 can be a workstation, a server computer, a router, a personal computer, portable computer, microprocessor-based entertainment appliance, a peer device or other common network node, and typically includes many or all of the elements described relative to computer 1802, although, for purposes of brevity, only memory/storage device 1834 is illustrated. The logical connections depicted include wired/wireless connectivity to a local area network (LAN) 1826 and/or larger networks, e.g., WAN 1824, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1802 can be connected to local network through a wired and/or wireless communication network interface or adapter 1820. Adapter 1820 can facilitate wired or wireless communication to LAN 1826, which can also include a wireless access point (AP) connected to the LAN 1826 for communicating with adapter 1820.

When used in a WAN networking environment, computer 1802 can include modem 1822 or can be connected to a communications server on WAN 1824 or has other means for establishing communications over WAN 1824, such as by way of the Internet. Modem 1822, which can be internal or external and a wired or wireless device, can be connected to system bus 1808 via input device interface 1818. In a networked environment, program modules depicted relative to computer 1802 or portions thereof, can be stored in a remote memory/storage device. It will be appreciated that the network connections shown are example and other means of establishing a communications link between the computers can be used.

Computer 1802 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 11 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 11BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)=$confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A device, comprising:
   a communication component configured to transmit one or more packets to one or more other devices on a communication network;
   a packet transmission queue that stores the one or more packets for transmission on the communication network;
   a data management queue that stores data items for submission to the packet transmission queue;
   at least one memory that stores computer executable instructions; and
   at least one processor that executes the computer executable instructions stored in the at least one memory, wherein the computer executable instructions comprise instructions that causes the at least one processor to:
   determine an expected arrival time to another device of a data item of the data items stored in the data management queue, determine that the expected arrival time exceeds a latest arrival time associated with the data item, wherein the latest arrival time is a function of a combination of a deadline for the data item and a timestamp for the data item,
   based on the determination that the expected arrival time exceeds the latest arrival time, remove the data item from the data management queue such that the data item is not submitted to the packet transmission queue and not transmitted on the communication network, and
   throttle the data items being placed in the data management queue based on a throttling criterion, wherein to throttle the data items the at least one processor reduces a sampling rate, reduces channels of data, or reduces types of data items for transmission.

2. The device of claim 1, wherein the computer executable instructions further comprise instructions that causes the at least one processor to: determine a size of the packet transmission queue; and in response to a determination that the size of the packet transmission queue has a defined relationship to a threshold size, forward another data item of the data items from the data management queue to the packet transmission queue.

3. The device of claim 1, wherein the computer executable instructions further comprise instructions that causes the at least one processor to: determine the expected arrival time of the data item to the other device based on a size of the packet transmission queue.

4. The device of claim 3, wherein the computer executable instructions further comprise instructions that causes the at least one processor to: determine the expected arrival time of the data item to the other device based on a number of additional data items of the data items that are ahead of the data item in the data management queue.

5. The device of claim 1, wherein the latest arrival time is based on a characteristic associated with the device.

6. The device of claim 1, wherein the latest arrival time is based on a characteristic associated with the other device.

7. The device of claim 1, wherein the latest arrival time is based on a type of data associated with the data item.

8. The device of claim 1, wherein the latest arrival time is based on a status of the device.

9. The device of claim 1, wherein the data management queue is a first in first out queue.

10. The device of claim 1, wherein the communication network is a Bluetooth® Low Energy (BLE) network.

11. The device of claim 1, wherein the device comprises a medical device.

12. The device of claim 1, further comprising one or more additional data management queues respectively configured to store the data items for submission to the packet transmission queue for transmission as the one or more packets on the communication network to the one or more other devices.

13. A method, comprising:
providing, by device comprising at least one processor, data items in a data management queue for buffering prior to submission to a packet transmission queue for transmission as one or more packets on a communication network to one or more other devices;
determining an expected arrival to another device of a data item of the data items stored in the data management queue;
determining that the expected arrival time is after a defined maximum acceptable arrival time associated with the data item, wherein the defined maximum acceptable arrival time is a first deadline for the data items in the data management queue added to a timestamp for the data item;
based on the determination that the expected arrival time is after the defined maximum acceptable arrival time, removing the data item form the data management queue such that the data item is not submitted to the packet transmission queue and not transmitted on the communication network; and
reducing, by the device, a rate of transferring the data items to the data management queue based on a determination that a size of the data management queue exceeds a threshold queue size, wherein the rate of transferring is reduced by reducing a sampling rate, reducing channels, or reducing types of data items included.

14. The method of claim 13, further comprising: determining, by the device, a size of the packet transmission queue; and supplying, by the device, another data item from the data management queue to the packet transmission queue, wherein the supplying is based on a determination that the size of the packet transmission queue is within a defined range of a threshold size.

15. The method of claim 14, further comprising selecting the other data item based on a priority associated with the other data item.

16. The method of claim 13, further comprising estimating the expected arrival time of the data item to the other device based on an expected transmission time per packet of the one or more packets in the packet transmission queue.

17. A non-transitory computer-readable storage medium storing executable instructions that, in response to execution, cause device comprising at least one processor to perform operations, comprising:
monitoring data items stored in a data management queue prior to submission of the data items to a packet transmission queue for transmission as one or more packets on a communication network to one or more other devices;
determining an expected arrival time to another device of a data item of the data items stored in the data management queue;
determining that the expected arrival time is after a defined latest arrival time for the data item, wherein the defined latest arrival time is a deadline for the data item added to a timestamp for the data item;
based on the determination that the expected arrival time is after the defined latest arrival time for the data item, removing the data item from the data management queue such that the data item is not submitted to the packet transmission queue and not transmitted on the communication network; and
reducing a rate of transferring the data items to the data management queue based on a determination that a size of the data management queue exceeds a threshold queue size, wherein the rate of transferring is reduced by reducing sampling rate, reducing channels, or reducing types of data items included.

18. The computer-readable storage medium of claim 17, wherein the operations further comprise: estimating a size of the packet transmission queue; and transferring another data item from the data management queue to the packet transmission queue based on an estimation that the size of the packet transmission queue is less than a threshold size.

19. A system comprising:
a sensor; and
a device, comprising:
a memory that stores computer executable instructions; and
at least one processor that executes the computer executable instructions stored in the memory, wherein the computer executable instructions comprise cause the at least one processor to:
detect a signal from the sensor; and
supply a data item of data items and corresponding to the signal to a data management queue for transmission to another device;
determine an expected arrival time to another device of a data item of the data item stored in the data management queue; determine that the expected arrival time exceeds an acceptable latest arrival time associated with the data item and also associated with a deadline for the data item;
remove the data item from the data management queue such that the data item is not submitted to a packet transmission queue and not transmitted to a communication network based on the determination that the expected arrival time exceeds the acceptable latest arrival time associated with the data item and also associated with the deadline for the data item; and
throttle the data items being placed in the data management queue based on a throttling criterion, wherein the fourth computer executable instruction to throttle reduces a sampling rate, reduces channels of data, or reduces types of data items for transmission.

20. The system of claim 19, further comprising the other device.

21. The system of claim 20, wherein the other device comprises a mobile device.

22. The system of claim 20, wherein the device further comprises a server device configured to receive the data item, or information about the data item, from the other device.

23. The system of claim 19, wherein the fourth computer executable instruction to throttle reduces a sampling rate of the signal to reduce a number of the data items to be supplied to the data management queue.

24. The system of claim 19, wherein the data items comprise marker data and waveform data, and the device further comprises a fifth computer executable instruction to remove waveform data from the data items to reduce a number of the data items to be supplied to the data management queue.

25. The device of claim 1, wherein the throttling criterion is based on a characteristic of the removed data item.

* * * * *